US012580054B2

(12) United States Patent
Tuysuzoglu et al.

(10) Patent No.: US 12,580,054 B2
(45) Date of Patent: Mar. 17, 2026

(54) COMPUTATIONALLY-EFFICIENT LOAD PLANNING SYSTEMS AND METHODS OF DIAGNOSTIC LABORATORIES

(71) Applicant: Siemens Healthcare Diagnostics Inc., Tarrytown, NY (US)

(72) Inventors: Ahmet Tuysuzoglu, Jersey City, NJ (US); Yue Zhang, Jersey City, NJ (US); Michael Heydlauf, Cary, NC (US); Luxi Zheng, Cary, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 232 days.

(21) Appl. No.: 18/044,614

(22) PCT Filed: Oct. 28, 2021

(86) PCT No.: PCT/US2021/072085
§ 371 (c)(1),
(2) Date: Mar. 9, 2023

(87) PCT Pub. No.: WO2022/104311
PCT Pub. Date: May 19, 2022

(65) Prior Publication Data
US 2023/0335235 A1      Oct. 19, 2023

Related U.S. Application Data

(60) Provisional application No. 63/198,787, filed on Nov. 13, 2020.

(51) Int. Cl.
G16H 10/40          (2018.01)

(52) U.S. Cl.
CPC .................................. G16H 10/40 (2018.01)

(58) Field of Classification Search
None
See application file for complete search history.

(56) References Cited

U.S. PATENT DOCUMENTS 5,154,314 A      10/1992  Van Wormer
5,641,006 A       6/1997  Autrey et al.
(Continued)

FOREIGN PATENT DOCUMENTS

CN      109416367 A      3/2019
CN      109476427 A      3/2019
(Continued)

OTHER PUBLICATIONS

Xirgo et al. Multi-Agent Model of a Sample Transport System for Modular In-Vitro Diagnostics Laboratories, Proceedings of 2012 IEEE 17th International Conference on Emerging Technologies & Factory Automation (ETFA 2012) (2012, pp. 1-8).*
(Continued)

*Primary Examiner* — David J Stoltenberg

(57) ABSTRACT

Systems and methods include an optimization-based load planning module including a data-reduction scheme for analyzers of bio-fluid samples. The optimization-based load planning module is executable on a computer server and is configured to optimize assay type assignments across a large number of analyzers based on one or more objectives, such as: load balancing, efficient reagent usage, reduced turn-around-time, reduced quality assurance costs, and/or improved system robustness. The optimization-based load planning module uses a data-reduction scheme to generate a load plan comprising computer-executable instructions configured to cause a system controller of a diagnostic laboratory system to assign each of the requested test types to be performed over the planning period to one or more selected (Continued)

analyzers in accordance with the one or more preferences or priorities. Other aspects are also described.

19 Claims, 9 Drawing Sheets

(56)                     References Cited

U.S. PATENT DOCUMENTS

| | | | |
|---|---|---|---|
| 5,653,862 | A | 8/1997 | Parris |
| 5,699,259 | A | 12/1997 | Colman et al. |
| 5,751,580 | A | 5/1998 | Chi |
| 5,890,134 | A | 3/1999 | Fox |
| 5,912,818 | A | 6/1999 | McGrady et al. |
| 5,983,198 | A | 11/1999 | Mowery et al. |
| 6,112,502 | A | 9/2000 | Frederick et al. |
| 6,115,640 | A | 9/2000 | Tarumi |
| 6,370,341 | B1 | 4/2002 | Haines |
| 6,463,346 | B1 | 10/2002 | Flockhart et al. |
| 6,788,997 | B1 | 9/2004 | Frederick |
| 7,029,922 | B2 | 4/2006 | Miller |
| 7,467,093 | B1 | 12/2008 | Newton et al. |
| 7,487,182 | B2 | 2/2009 | Kataria et al. |
| 7,552,071 | B2 | 6/2009 | Tirinato et al. |
| 7,685,026 | B1 | 3/2010 | McGrady et al. |
| 8,296,170 | B2 | 10/2012 | O'Brien et al. |
| 8,306,838 | B2 | 11/2012 | Heise et al. |
| 8,423,180 | B1 | 4/2013 | Frederick et al. |
| 8,951,805 | B2 | 2/2015 | Fritchie et al. |
| 9,261,523 | B2 | 2/2016 | Fritchie et al. |
| 9,335,336 | B2 | 5/2016 | Silbert et al. |
| 9,740,897 | B1 | 8/2017 | Salour |
| 9,779,588 | B2 | 10/2017 | Angus et al. |
| 9,848,774 | B2 | 12/2017 | Bergstrom et al. |
| 9,864,351 | B2 | 1/2018 | Slupik et al. |
| 10,024,734 | B2 | 7/2018 | Tirinato et al. |
| 10,072,962 | B2 | 9/2018 | Ismail et al. |
| 10,082,517 | B2 | 9/2018 | Ackermann et al. |
| 10,338,086 | B2 | 7/2019 | Maetzler et al. |
| 10,817,832 | B1 | 10/2020 | Agrawal et al. |
| 10,867,274 | B2 | 12/2020 | Jones et al. |
| 10,872,307 | B2 | 12/2020 | Mickles et al. |
| 11,068,844 | B2 | 7/2021 | Smith et al. |
| 11,150,256 | B2 | 10/2021 | Ackermann et al. |
| 2001/0013247 | A1 | 8/2001 | Wilson et al. |
| 2002/0010659 | A1 | 1/2002 | Cruse et al. |
| 2002/0082957 | A1 | 6/2002 | Krassi |
| 2002/0107642 | A1 | 8/2002 | Nishida et al. |
| 2003/0115088 | A1 | 6/2003 | Thompson |
| 2003/0149759 | A1 | 8/2003 | Hetherington et al. |
| 2003/0172009 | A1 | 9/2003 | Katou et al. |
| 2004/0220844 | A1 | 11/2004 | Sanville et al. |
| 2005/0049942 | A1 | 3/2005 | Richard et al. |
| 2005/0227360 | A1 | 10/2005 | Devlin, Sr. |
| 2005/0242181 | A1 | 11/2005 | Cunningham et al. |
| 2006/0030049 | A1 | 2/2006 | Bhimani et al. |
| 2006/0178568 | A1 | 8/2006 | Danna et al. |
| 2006/0247985 | A1 | 11/2006 | Liamos et al. |
| 2008/0025734 | A1 | 1/2008 | Kehoe et al. |
| 2008/0065264 | A1 | 3/2008 | Omura et al. |
| 2008/0113440 | A1* | 5/2008 | Gurney .................. G01N 1/312 422/65 |
| 2008/0167976 | A1 | 7/2008 | Chuang et al. |
| 2008/0235055 | A1 | 9/2008 | Mattingly et al. |
| 2008/0240988 | A1 | 10/2008 | Wakamiya et al. |
| 2009/0119142 | A1 | 5/2009 | Yenni et al. |
| 2009/0281930 | A1 | 11/2009 | Sakagami |
| 2009/0326829 | A1 | 12/2009 | Liamos et al. |
| 2010/0042439 | A1 | 2/2010 | Martinez et al. |
| 2010/0082483 | A1 | 4/2010 | Sanders et al. |
| 2010/0204557 | A1 | 8/2010 | Kiaie et al. |
| 2010/0322822 | A1 | 12/2010 | Fritchie et al. |
| 2010/0324722 | A1 | 12/2010 | Fritchie et al. |
| 2011/0044854 | A1* | 2/2011 | Devlin, Sr. ........ G01N 35/0092 422/64 |
| 2011/0245089 | A1* | 10/2011 | Scott ...................... G16H 10/40 435/5 |
| 2011/0246215 | A1 | 10/2011 | Postma et al. |
| 2012/0232520 | A1 | 9/2012 | Sloan et al. |
| 2012/0283867 | A1 | 11/2012 | Gelbman et al. |
| 2012/0296769 | A1 | 11/2012 | Ginster et al. |
| 2014/0048556 | A1 | 2/2014 | Pearcy et al. |
| 2014/0100139 | A1* | 4/2014 | Barnes ............... G01N 35/0095 702/121 |
| 2014/0129172 | A1* | 5/2014 | Eberhardt .......... G01N 35/0092 702/108 |
| 2014/0337040 | A1 | 11/2014 | Debusk et al. |
| 2015/0338427 | A1* | 11/2015 | Pollack .............. G01N 35/0095 422/67 |
| 2016/0341752 | A1* | 11/2016 | Holmes .............. G01N 35/0092 |
| 2018/0080949 | A1* | 3/2018 | Jost .................. G06Q 10/06316 |
| 2018/0082038 | A1 | 3/2018 | Blair et al. |
| 2018/0340949 | A1 | 11/2018 | Maetzler et al. |
| 2018/0372648 | A1 | 12/2018 | Wissmann et al. |
| 2019/0041318 | A1 | 2/2019 | Wissmann et al. |
| 2019/0178680 | A1 | 6/2019 | Kriss |
| 2019/0206007 | A1 | 7/2019 | Leach |
| 2020/0013501 | A1 | 1/2020 | Page et al. |
| 2020/0057998 | A1 | 2/2020 | Ophardt et al. |
| 2020/0271683 | A1 | 8/2020 | Ha et al. |
| 2020/0319219 | A1* | 10/2020 | Vansickler ......... G01N 35/0092 |
| 2020/0334614 | A1 | 10/2020 | Javaid et al. |
| 2021/0132093 | A1* | 5/2021 | Furrer ............... G01N 35/0092 |
| 2022/0293226 | A1* | 9/2022 | Tuysuzoglu ........... G16H 40/20 |

FOREIGN PATENT DOCUMENTS

| | | | |
|---|---|---|---|
| EP | 3299794 A1 | 3/2018 | |
| WO | 2019126033 A1 | 6/2019 | |
| WO | 2019156828 A1 | 8/2019 | |
| WO | WO 2020/106696 A1 * | 11/2019 | ............. G16H 10/40 |
| WO | 2020106693 A1 | 5/2020 | |
| WO | 2021015854 A1 | 1/2021 | |
| WO | 2021015881 A1 | 1/2021 | |

OTHER PUBLICATIONS

Wolf et al. Device Integration Concepts in Laboratory Automation, INES 2020 • 24th International Conference on Intelligent Engineering Systems • Jul. 8-10, 2020 • Reykjavik, Iceland.*

Anonymous: "Approximation algorithm—Wikipedia"; Oct. 26, 2020 (Oct. 26, 2020), pp. 1-7, XP093142429, Retrieved from the Internet: URL: https://en.wikipedia.org/w/index.php?title=Approximation_algorithm&oldid=985557338 [retrieved on Mar. 18, 2024].

International Search Report and Written Opinion of International Application No. PCT/US2021/072085 dated Jan. 31, 2022.

Garg H. et. al. "Multi-objective reliability-redundancy allocation problem using particle swarm optimization" Computers & Industrial engineering 64:247-255 (2013).

Pedroso J. et. al. "Mathematical Optimization Documentation" GitHub (2017).

Sepulveda J. et. al. "The ideal laboratory information system" Archives of Pathology and Laboratory Medicine 137.8:1129-1140 (2013).

Smith Cole J. et al.; "A tutorial guide to mixed-integer programming models and solution techniques"; University of Florida; Mar. 26, 2007; Retrieved on Aug. 18, 2020 from the Internet: <URL: http://www.ie.boun.edu.tr/-taskin/pdf/IP_tutorial.pdf>; pp. 1-23.

Sonmez Hakan; "Reagent usage optimization in high volume diagnostics testing"; Massachusetts Institute of Technology, MBA and MS Thesis; Jun. 7, 2018; retrieved on Aug. 9, 2020 from the Internet: <URL:https://dspace.mit.edu/b1tstream/handle/1721.1/117968/1051237853-MIT.pdf?>; pp. 1-68.

Results from the National Survey of Independent and Community Clinical Laboratories, Nov. 14, 2021, by George Washington University.

Yu Yong et al: "Research on the linear evaluation scheme and mathematical operation procedure for quantitative determination of

(56) References Cited

OTHER PUBLICATIONS in vitro diagnostic reagents—Series research on in vitro diagnostic reagent products (V)"; Apr. 15, 2011; Capital Medicine; Issue 08.

* cited by examiner

400A

| A 404 | | | | 407 | |
|---|---|---|---|---|---|
| A | B | C | - | - | - |

| A 406 | | | | | |
|---|---|---|---|---|---|
| D | E | F | - | - | - |

| A 408 | | | | | |
|---|---|---|---|---|---|
| G | H | I | - | - | - |

PRIOR ART

| A 404 | | | | | |
|---|---|---|---|---|---|
| A | B | C | D | E | F |

| 407 | A 406 | | | | |
|---|---|---|---|---|---|
| D | E | F | G | H | I |

| A 408 | | | | | |
|---|---|---|---|---|---|
| G | H | I | A | B | C |

PRIOR ART

| A 404 | | | | | |
|---|---|---|---|---|---|
| A | B | C | G | H | - |

| A 406 | | | | | |
|---|---|---|---|---|---|
| D | E | F | G | - | - |

| 407 | A 408 | | | | |
|---|---|---|---|---|---|
| D | A | I | G | - | - |

```
┌─────────────────────────────────────────┐
│   Receiving, At A Computer Server, Computer-
│    readable Data Comprising An Inventory Of
│         A Plurality Of Analyzers Included
│  In The Diagnostic Laboratory System, Test Types
│  And Numbers Of Requested Tests To Be Performed      ~502
│      By The  Diagnostic Laboratory System, And
│  Preferences Or Priorities Related To Operation Of
│    The  Diagnostic Laboratory System And To The
│   Test Types And Numbers Of The Requested Tests
│                  To Be Performed
└─────────────────────────────────────────┘
```

```
┌─────────────────────────────────────────┐
│      Determining, Via An Optimization-Based Load
│  Planning Module Executing On The Computer Server,
│    A Load Plan For Performing Each Of The Requested
│     Tests In The Diagnostic Laboratory System, The
│        Load Plan Comprising Computer Executable
│       Instructions Configured To Cause A System       ~504
│  Controller Of The Diagnostic Laboratory System To
│   Assign Each Of The Requested Test Types To Be
│   Performed At One Or More Selected Analyzers Of
│   The Diagnostic Laboratory System In Accordance
│  With One Or More Of The Preferences Or Priorities
└─────────────────────────────────────────┘
```

Figure 7:
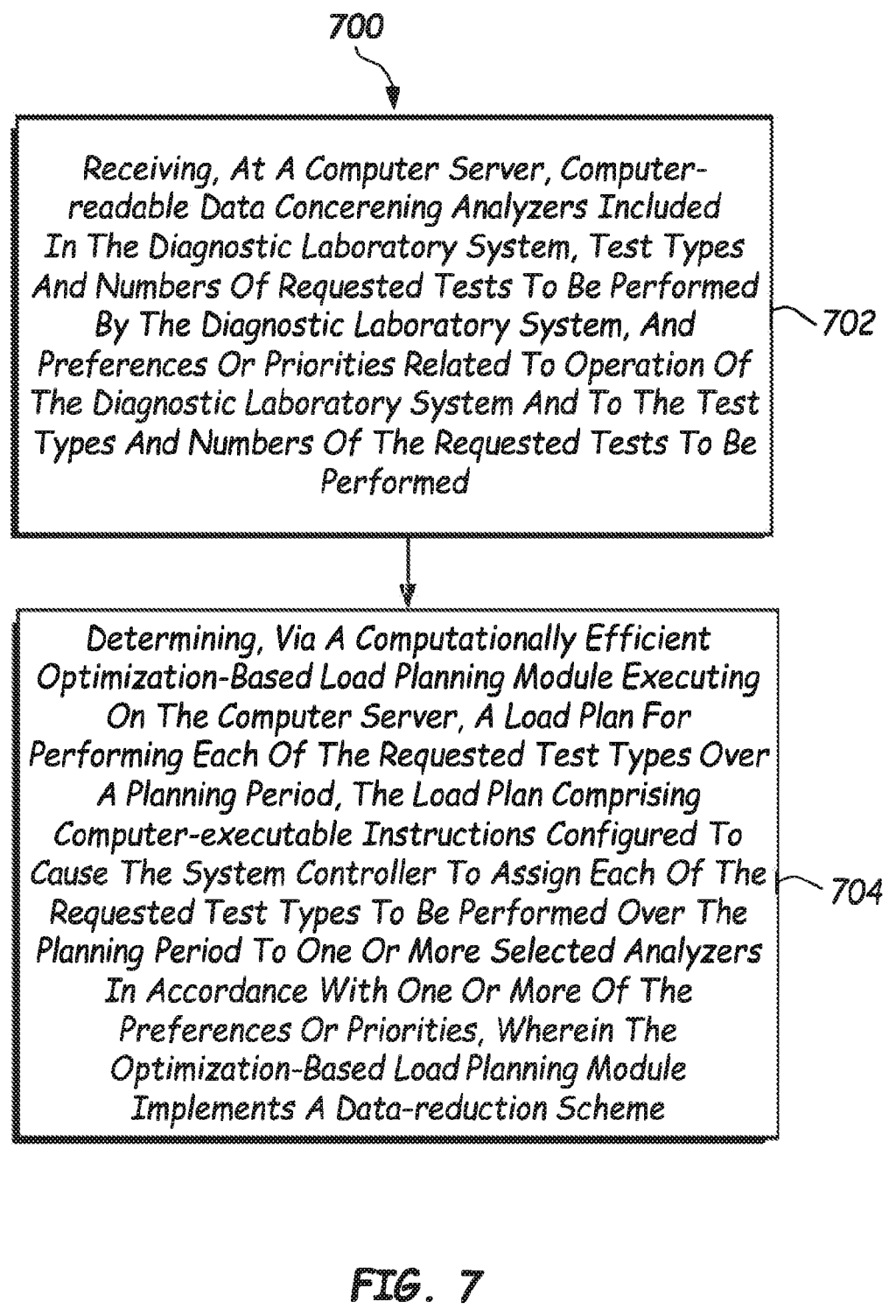

Receiving, At A Computer Server, Computer-readable Data Concerening Analyzers Included In The Diagnostic Laboratory System, Test Types And Numbers Of Requested Tests To Be Performed By The Diagnostic Laboratory System, And Preferences Or Priorities Related To Operation Of The Diagnostic Laboratory System And To The Test Types And Numbers Of The Requested Tests To Be Performed

702

Determining, Via A Computationally Efficient Optimization-Based Load Planning Module Executing On The Computer Server, A Load Plan For Performing Each Of The Requested Test Types Over A Planning Period, The Load Plan Comprising Computer-executable Instructions Configured To Cause The System Controller To Assign Each Of The Requested Test Types To Be Performed Over The Planning Period To One Or More Selected Analyzers In Accordance With One Or More Of The Preferences Or Priorities, Wherein The Optimization-Based Load Planning Module Implements A Data-reduction Scheme

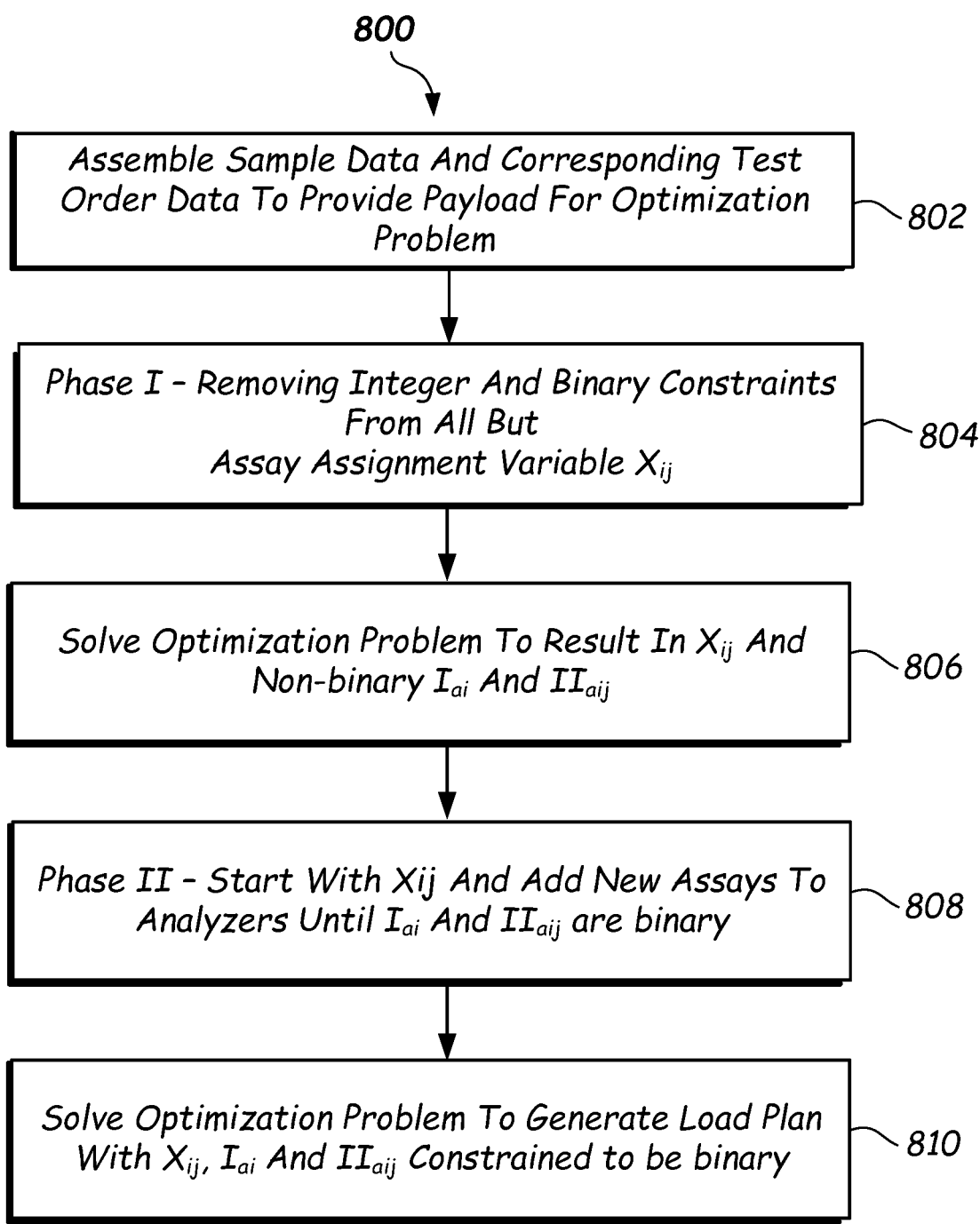

*800*

*Assemble Sample Data And Corresponding Test Order Data To Provide Payload For Optimization Problem* — *802*

*Phase I – Removing Integer And Binary Constraints From All But Assay Assignment Variable $X_{ij}$* — *804*

*Solve Optimization Problem To Result In $X_{ij}$ And Non-binary $I_{ai}$ And $II_{aij}$* — *806*

*Phase II – Start With Xij And Add New Assays To Analyzers Until $I_{ai}$ And $II_{aij}$ are binary* — *808*

*Solve Optimization Problem To Generate Load Plan With $X_{ij}$, $I_{ai}$ And $II_{aij}$ Constrained to be binary* — *810*

*FIG. 8*

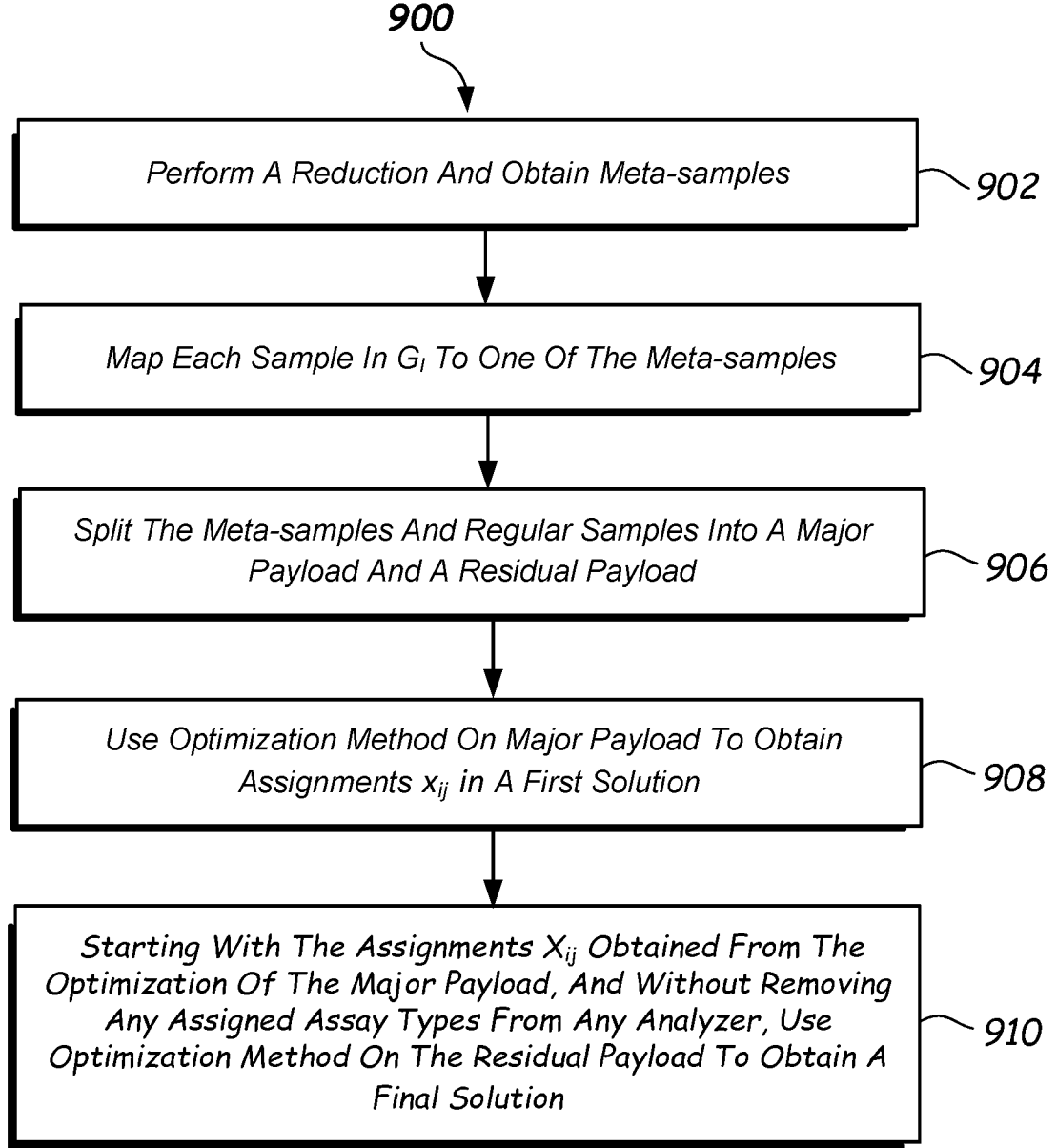

*900*

Perform A Reduction And Obtain Meta-samples      ~*902*

Map Each Sample In $G_l$ To One Of The Meta-samples      ~*904*

Split The Meta-samples And Regular Samples Into A Major Payload And A Residual Payload      ~*906*

Use Optimization Method On Major Payload To Obtain Assignments $x_{ij}$ in A First Solution      ~*908*

Starting With The Assignments $X_{ij}$ Obtained From The Optimization Of The Major Payload, And Without Removing Any Assigned Assay Types From Any Analyzer, Use Optimization Method On The Residual Payload To Obtain A Final Solution      ~*910*

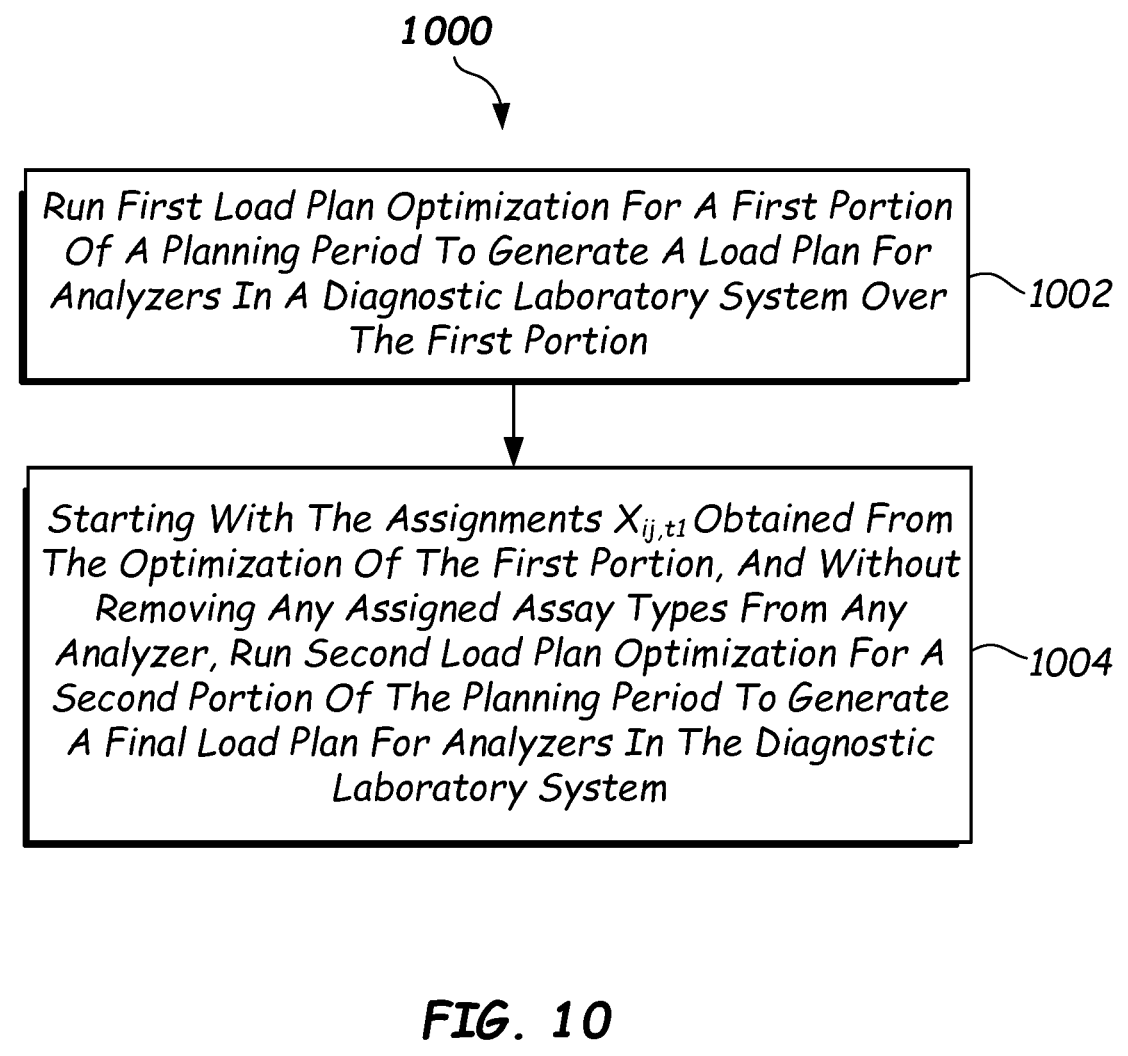

Run First Load Plan Optimization For A First Portion Of A Planning Period To Generate A Load Plan For Analyzers In A Diagnostic Laboratory System Over The First Portion ⌐1002

Starting With The Assignments $X_{ij,t1}$ Obtained From The Optimization Of The First Portion, And Without Removing Any Assigned Assay Types From Any Analyzer, Run Second Load Plan Optimization For A Second Portion Of The Planning Period To Generate A Final Load Plan For Analyzers In The Diagnostic Laboratory System ⌐1004

*FIG. 10*

COMPUTATIONALLY-EFFICIENT LOAD PLANNING SYSTEMS AND METHODS OF DIAGNOSTIC LABORATORIES

CROSS REFERENCE TO RELATED APPLICATIONS

This disclosure is a 371 of PCT/US2021/072085, filed Oct. 28, 2021, which claims the benefit of U.S. Provisional Patent Application No. 63/198,787, filed Nov. 13, 2020, the disclosures of which are hereby incorporated by reference in their entireties for all purposes.

FIELD

This disclosure relates to systems and methods that provide load planning for analyzers of diagnostic laboratories.

BACKGROUND

Centralization and consolidation of multiple small-scale diagnostic laboratories into large-scale diagnostic laboratories for the analysis of bio-fluid samples (e.g., blood, blood plasma or serum, urine, etc.) has been a trend in recent years. This trend is driven primarily by reductions in reimbursements by government health insurers for the most frequently ordered laboratory tests. In view of typically small profit margins, continued operation by many small-scale diagnostic laboratories may not be possible, especially if reimbursement rates continue to drop. Moreover, government reporting requirements for information regarding payer rates and associated test volumes of diagnostic laboratories may necessitate an information technology infrastructure that many small-scale diagnostic laboratories do not have the means to implement. Thus, centralization and consolidation of small-scale diagnostic laboratories into large-scale diagnostic laboratories as a trend is likely to continue.

Large-scale diagnostic laboratories may process millions of bio-fluid samples each year across a large number of analyzers (e.g., 100+) in a diagnostic laboratory. The large number of laboratory analyzers may be connected via automated tracks extending, e.g., to a length of 200 meters or more. The operation of such large-scale diagnostic laboratories requires substantial computer processing power.

Accordingly, there is an unmet need to improve large-scale diagnostic laboratories that include a large number of analyzers.

SUMMARY

According to a first aspect, a method of load planning in a diagnostic laboratory system is provided. The method includes receiving, at a computer server, computer-readable data concerning analyzers included in the diagnostic laboratory system, and test types and numbers of tests to be performed within the diagnostic laboratory system over a planning period, and preferences or priorities related to operation of the diagnostic laboratory system and to the test types and numbers of the requested tests to be performed; and determining, via an optimization-based load planning module including a data-reduction scheme executing on the computer server, a load plan for performing each of the requested test types over the planning period, the load plan comprising computer-executable instructions configured to cause a system controller to assign each of the requested test types to be performed over the planning period to one or more selected analyzers in accordance with the one or more preferences or priorities (objectives).

In a further aspect, a diagnostic laboratory system is provided. The diagnostic laboratory system includes a system controller; a plurality of analyzers connected to each other via one or more automated tracks for transporting sample containers to and from the plurality of analyzers under the control of the system controller, each of the plurality of analyzers configured to perform one or more tests on one or more samples contained in the sample containers over a planning period; and a computer server coupled to the system controller, the computer server comprising an optimization-based load planning module including a data-reduction scheme executing on the computer server, a load plan for performing each requested test type over the planning period, the load plan comprising computer executable instructions configured to cause a system controller to assign each of the requested test types to be performed over the planning period to one or more selected analyzers in accordance with the one or more preferences or priorities.

According to another aspect, a non-transitory computer-readable storage medium is provided. The non-transitory computer-readable storage medium comprises an optimization-based load planning module including a data-reduction scheme having computer-executable instructions configured to cause a computer server to: determine a load plan for performing each of the requested test types over a planning period, the load plan comprising computer-executable instructions configured to cause a system controller to assign each of the requested test types to be performed over the planning period to one or more selected analyzers in accordance with the one or more preferences or priorities.

Still other aspects, features, and advantages of this disclosure may be readily apparent from the following description and illustration of a number of example embodiments and implementations, including the best mode contemplated for carrying out the invention. This disclosure may also be capable of different embodiments, and its several details may be modified in various respects, all without departing from the scope of the disclosure. This disclosure is intended to cover all modifications, equivalents, and alternatives falling within the scope of the claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the disclosure in any way.

FIGS. 4A-B illustrate example load plans for a diagnostic laboratory system according to the prior art.

FIG. 4C illustrates an example load plan for a diagnostic laboratory system according to one or more embodiments.

FIG. 5 is flowchart of a method of optimization-based load planning for a diagnostic laboratory system according to one or more embodiments.

FIG. 7 is flowchart of a computationally-efficient method of optimization-based load planning for a diagnostic laboratory system according to one or more embodiments.

FIG. 8 is flowchart of a first embodiment of a computationally-efficient method of optimization-based load planning for a diagnostic laboratory system using a surrogate optimization method according to one or more embodiments.

FIG. 9 is flowchart of a second embodiment of a computationally-efficient method of optimization-based load planning for a diagnostic laboratory system using sample grouping according to one or more embodiments.

FIG. 10 is flowchart of a third embodiment of a computationally-efficient method of optimization-based load planning for a diagnostic laboratory system using iterative optimization according to one or more embodiments.

DETAILED DESCRIPTION

Figure 1:
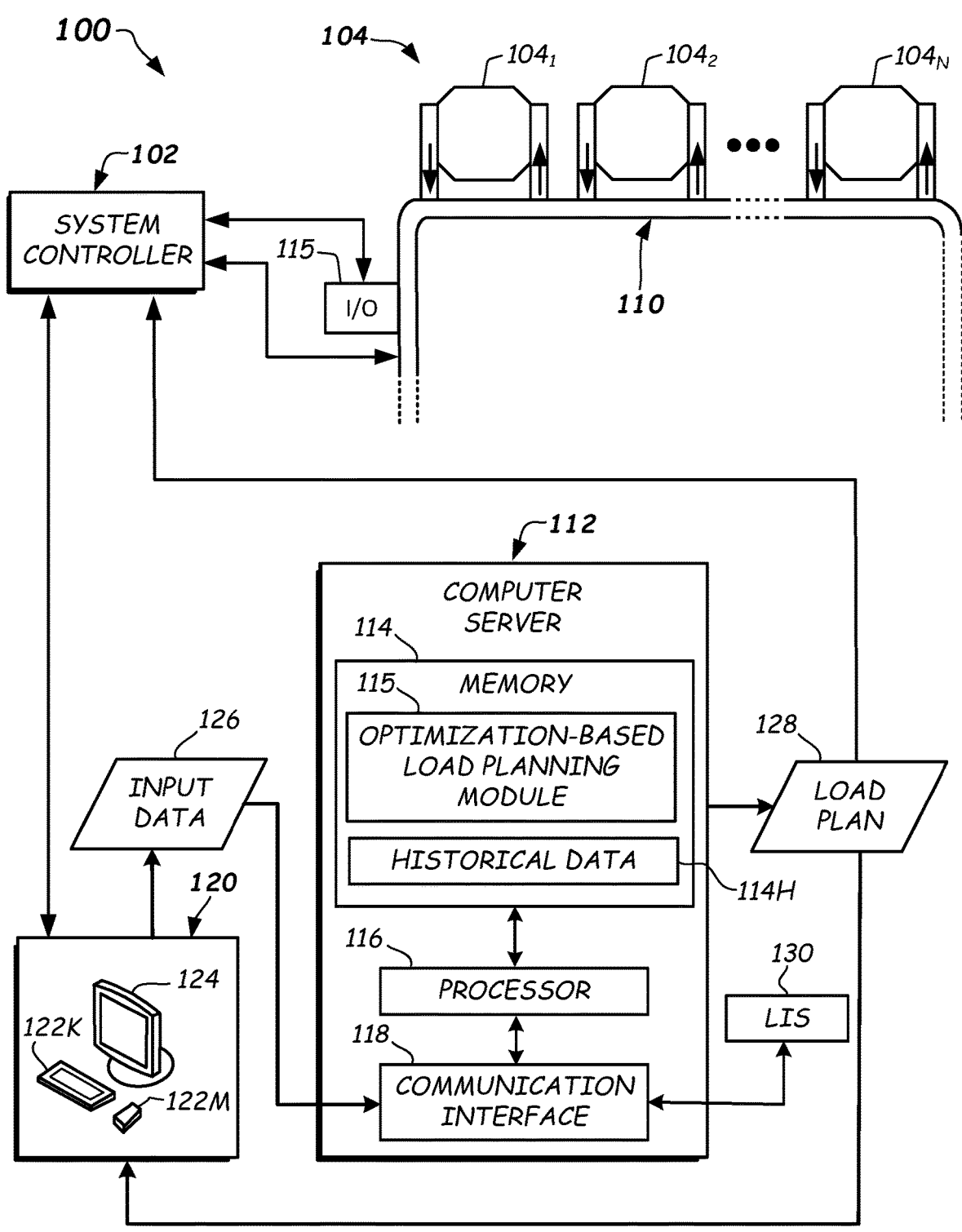
FIG. 1 illustrates a schematic block diagram of a diagnostic laboratory system according to one or more embodiments.

Compared to small-scale diagnostic laboratory systems where only a limited number of analyzers are used, it may be possible to improve efficiency of large-scale diagnostic laboratory systems using a multitude of analyzers, especially that have overlapping test menus (e.g., assay and/or clinical chemistry test menus). In particular, there is an unmet need to improve operational efficiency of large-scale diagnostic laboratories by creating an optimized assignment of tests to analyzers (optimized load plan) that have been ordered on samples (e.g., assays and/or clinical chemistry) across the multiple analyzers, wherein the optimized assignment is carried out via an optimization method. However, the inventors have discovered that implementing such optimization methods in large-scale diagnostic laboratories may impose substantial computational burdens, which may become impractical in very large-scale systems, as the computing power needed for such optimization becomes cost prohibitive and/or the time to perform the load plan optimization may take weeks or even longer. In extremely large-scale systems, it may be impossible to perform an optimization, as the variables can number in the billions, such that there may even be insufficient storage for them. Thus, diagnostic laboratory systems utilizing optimization methods according to embodiments of this disclosure are configured to optimize such test assignments across a large number of analyzers, such as immuno-assay instruments, clinical chemistry analyzers, and in vitro analyzers, yet do so in a computationally-efficient manner.

The computational efficiency of the optimization systems and methods may be improved, especially in diagnostic laboratory systems having large-scale sample throughput, by implementing a data-reduction scheme by: 1) solving successive surrogate optimization problems, 2) grouping of common test order patterns so that samples can be represented by meta-samples, or 3) by iteratively optimizing over successive time periods within a planning period, or 4) any combination of the aforementioned data-reduction schemes 1-3.

Further details of the computationally-efficient load plan optimization systems and methods will be described with reference to FIGS. 1-10 herein.

In order to describe the computationally-efficiency optimization systems and methods herein, embodiments of optimization systems and methods that have not been optimized for computational efficiency will first be described. Such optimization systems and methods that have not been optimized for computational efficiency are referred to herein as being "standard optimization systems" and "standard optimization methods" These standard optimization systems and standard optimization methods have been described in U.S. Provisional Patent Application No. 62/877,885 to Ahmet Tuysuzoglu filed on Jul. 24, 2019, and entitled "Optimization-Based Load Planning Systems For Laboratory Analyzers," and in PCT patent application PCT/US20/35507 filed Jun. 1, 2020, and entitled "Optimization-Based Load Planning Systems And Methods For Laboratory Analyzers."

Standard Optimization Systems & Methods

Standard optimization systems and standard optimization methods provide a load plan for scheduling (assigning) tests to a plurality of analyzers in a diagnostic laboratory system over a planning period. Such standard optimization systems and methods can advantageously provide one or more of the following five priorities:

load balancing,
 efficient reagent usage,
 reduced turn-around-time (TAT),
 lower quality assurance costs, and/or
 improved system robustness.

Reducing TAT can increase system throughput, staying within limits of service-level agreements, and responding to time-sensitive requests (e.g., STAT requests). Providing load balancing across each analyzer can improve overall TAT and reduce excessive analyzer wear-out. Reagents may be added to samples to help determine, measure, or identify a characteristic or condition of the sample (e.g., measure an amount of glucose or other analyte in a blood sample). Reagents can be a large cost associated with diagnostic laboratory system operation. Thus, optimizing reagent use may be a priority in some diagnostic laboratory system operations. Also, each analyzer goes through quality control and calibration procedures that incur both time and costs. Thus managing the use of analyzers for optimal efficiency leads to lower quality assurance costs and improved time efficiency. Finally, ensuring robustness of the setup of the entire diagnostic laboratory system increases the likelihood that all requested testing can be completed, even if one or more analyzer is offline, such as for maintenance or repair.

The standard optimization systems and methods described below can implement the optimization of test assignments across the analyzers as a mixed integer linear program (MILP) that can be tailored to the unique needs of a particular diagnostic laboratory system. For example, if TAT is a desired objective (goal), one or more embodiments of the standard optimization systems and methods can be configured to prioritize TAT as an objective over other considerations. Furthermore, the standard optimization systems and methods can be utilized continuously to adapt to changing demands of workloads of the diagnostic laboratory system, such as, e.g., spikes in requests for certain tests.

Standard optimization systems and methods according to embodiments include configurable objective functions and constraint functions that can be tailored to the unique needs of any particular diagnostic laboratory system. Constraints may include, but not limited to, for example:

the number of available reagent pack slots (e.g., wedges-
  locations that receive a reagent pack or container) in a
  reagent carousel of each analyzer,
 initial reagent pack volumes, and
 configuration of test menus for each analyzer.

Objective functions may include, e.g., workload balancing across the analyzers (load balancing), optimizing reagent use to reduce reagent cost, reduced turn-around-time (TAT), such as to minimize a total number visits to analyzers that samples have to make to complete required tests (e.g., some samples may have to visit three or more analyzers to complete their required testing, while other samples may have to visit only one analyzer to complete their required testing), reduced quality assurance (QA) costs, and providing test assignment redundancy to provide improved system robustness.

Standard optimization systems and methods according to embodiments may be configured to find an optimal assignment, based on input such as historical data from a previous similar planning period or the current workload of the diagnostic laboratory system. Thus, a selection of an operation window (a planning period) of the analyzers can be based on time or the number of samples to be processed. Standard optimization systems and methods can report assay results and the number of assays that cannot be run to completion because of insufficient reagent; allow easy addition of possible new constraints to an existing diagnostic laboratory system, allow prioritization of objectives with respect to an order of importance, relative normalized weights, or a combination of the two; and/or simulate and observe the effects of enabled/disabled constraints and/or objective prioritization on key performance metrics.

In some embodiments, the standard optimization systems and methods may provide an extension that can report the required number of reagent packs to install for each assay type and for each analyzer, so the workload can be run to completion over the planning period.

FIG. 1 illustrates a standard diagnostic laboratory system 100 according to embodiments. Standard diagnostic laboratory system 100 may include a system controller 102, a plurality of analyzers 104 (represented by analyzers 1041, 1042, and 104N), one or more automated tracks 110, a computer server 112, sample container loading area such as input/output (I/O) device 115, and a user interface 120. Standard diagnostic laboratory system 100 may include other components, equipment, and devices (not shown), such as, e.g., various sensors, barcode readers, robotic mechanisms, pre-processing stations (which may include, e.g., an automated centrifuge and sample pre-screening equipment), and the like.

Automated track 110 may be configured to transport sample containers (not shown) to and from each of the analyzers 104 as well as to and from other locations within the standard diagnostic laboratory system 100. Sample containers may each be provided with one or more labels that may include identification information thereon, such as, a timestamp, requested test(s), patient identification, etc. The label(s) may further include, e.g., a barcode and/or have alphanumeric information printed thereon that may be machine readable at various locations about standard diagnostic laboratory system 100. Automated track 110 may be a railed track (e.g., a mono rail or a multiple rail), a collection of conveyor belts, conveyor chains, moveable platforms, or any other suitable type of conveyance mechanism. Automated track 110 may be circular or other suitable shape and may be a closed track (e.g., an endless track).

System controller 102 may control the operation of the standard diagnostic laboratory system 100 including movement of sample containers to and from each analyzer 104 and elsewhere throughout the standard diagnostic laboratory system 100, and operation of various other system components (and those not shown). Certain aspects of the operation of each analyzer 104 for carrying out various types of testing may be controlled by system controller 102. However, each analyzer 104 may include its own work station (not shown) configured to control the testing carried on thereat. System controller 102 may include, e.g., a microprocessor-based central processing unit or other suitable processor, a suitable memory, and software and/or firmware, and other suitable electronics and hardware for controlling the operation of standard diagnostic laboratory system 100.

Analyzers 104 are configured to perform one or more types of diagnostic tests on biological samples, such as, e.g., whole blood, serum or plasma, urine, cerebral-spinal fluid, etc. In some embodiments, standard diagnostic laboratory system 100 may have many analyzers, each representing any inventory-consuming diagnostic discipline, such as, e.g., clinical chemistry, immuno-assay, hematology, or molecular. In some embodiments, many analyzers 104 of the standard diagnostic laboratory system 100 may be capable of performing the same menu of tests, while other analyzers 104 may be capable of performing only a limited number of tests, or only certain individual tests. Some of the testing performed by the analyzers 104 of standard diagnostic laboratory system 100 may include, but not limited to, e.g., glucose, Hemoglobin A1C, sodium, potassium, chloride, carbon dioxide, cholesterol, triglyceride, Pro Time, iron, lipase, bilirubin, calcium, magnesium, creatinine, urea nitrogen, thyroid stimulating hormone, hepatitis A, and/or hepatitis B, and the like. Other testing may be performed by the analyzers 104 of the standard diagnostic laboratory system 100.

Figure 2:
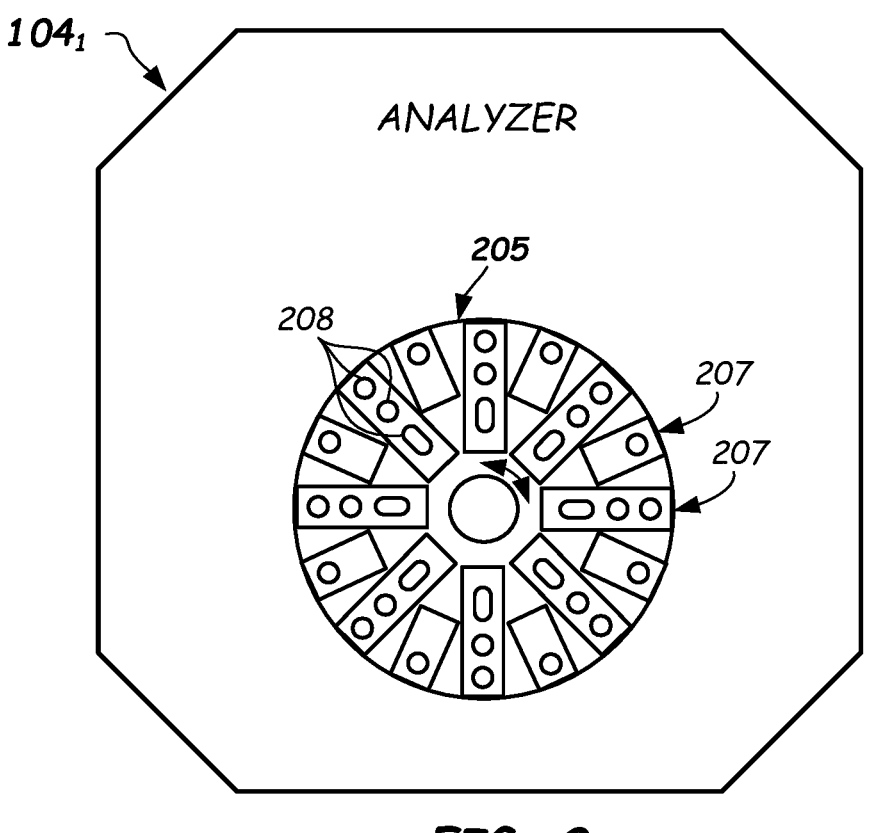
FIG. 2 illustrates a schematic diagram of a laboratory analyzer having a reagent carousel according to one or more embodiments.

As shown in FIG. 2, at least some analyzers, such as analyzer 1041, can include a reagent carousel 205 that has a plurality of slots 207 (e.g., locations) that are configured to contain reagents containers (e.g., reagent packs) therein. The reagents may be added to test samples to help determine, measure, or identify a characteristic or condition of the test sample (e.g., measure an amount of iron, glucose or other analyte or constituent in the sample). The reagent slots 207 may be arranged radially around the center of reagent carousel 205 such that a gantry or other robot including a pipette (neither shown) may access any one of the reagents positioned in a reagent slot 207 via rotation of reagent carousel 205. Each of slots 207 may receive a same reagent or a different reagent. The number of slots 207 in reagent carousel 205 may differ across laboratory analyzers. Different types of reagent packs or cartridges containing different numbers of access locations 208 may be used. Further, reagent packs or cartridges containing access locations 208 may be located or held in slots 207 in other types of dispensing implements, such as drawers, trays, or platforms. Slot 207 as used herein means any location of an analyzer that is configured to receive a reagent pack or reagent container thereat.

Returning again to FIG. 1, user interface 120 may be communicatively coupled to system controller 102 and to computer server 112. User interface 120 may include a user input device (e.g., keyboard) 122K and/or mouse 122M for entering, e.g., data, requests for status, operational and control commands, such as objectives and constraints, weights, etc., to system controller 102 and/or to computer server 112. User interface 120 may also include a display device 124, such as display screen shown, configured to display status, menus, data, and/or messages received from system controller 102 and computer server 112. For example, user interface 120 may provide information about the operational status of analyzers 104 as well as information regarding the status of tests being performed or to be performed thereat. In some embodiments, user interface 120 may include a touch screen user input device.

Computer server 112, which in some embodiments may be a cloud-based server or servers, may be any suitable computer device or collection of devices, and includes a memory 114 (e.g., RAM, ROM, other, or combinations) configured to store programming instructions and other information/data. Computer server 112 may also include a processor 116 (e.g., a CPU, microprocessor, or the like) configured to execute programming instructions. Computer server 112 may further include a communication interface 118 via which computer server 112 may be coupled to and in electronic communication with system controller 102 and user interface 120. In some embodiments, communication interface 118 may enable communication with a network (not shown) coupled between computer server 112 and system controller 102 and/or user interface 120. The network may include, e.g., the Internet, a local area network (LAN), a wireless local area network (WLAN), a power line communication (PLC) network, or the like. Communication interface 118 may be configured to receive input data 126 from user interface 120.

Computer server 112 may also include an optimization-based load planning module 115, described in more detail below. The optimization-based load planning module 115 may be stored in memory 114 and executed by processor 116. In alternative embodiments, the optimization-based load planning module 115 may be stored in other non-transitory computer readable storage mediums. The optimization-based load planning module 115 includes computer-executable instructions and may be configured and operable to receive and process input data 126 to create an optimized load plan 128 as an output. Load plan input data 126 includes computer-readable data representing at least an inventory of the plurality of analyzers 104 included in the diagnostic laboratory system 100, types and numbers of requested tests to be performed by diagnostic laboratory system 100 over the planning period, and preferences or priorities (objectives) related to operation of diagnostic laboratory system 100 and to the types and numbers of requested tests to be performed. Such preferences and priorities can be provided as objective functions and constraint functions of the standard optimization method.

Figure 3:
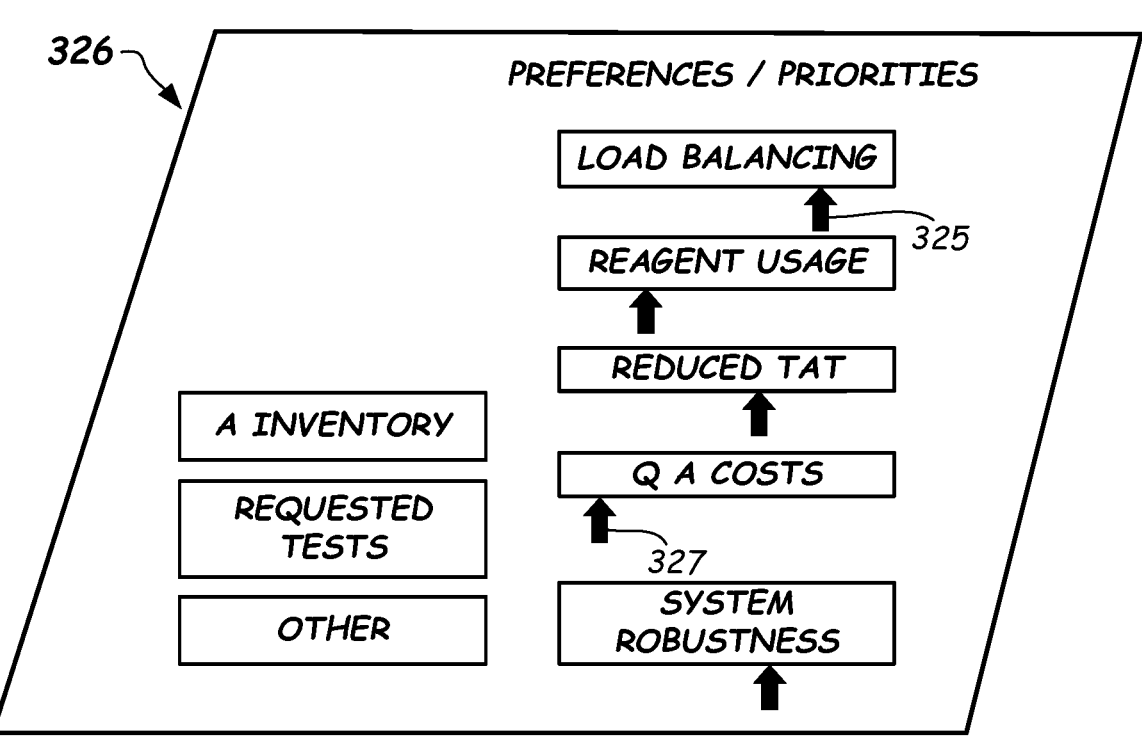
FIG. 3 illustrates a functional block diagram of input data for an optimization-based load planning module according to one or more embodiments.

FIG. 3 illustrates input data 326, which is an embodiment of input data 126 and may be provided as input to the optimization-based load planning module 115 in accordance with one or more embodiments herein. The inventory data of analyzers (laboratory analyzer (LA) Inventory) may indicate and quantify, e.g., the total number of available analyzers 104, types of tests each analyzer 104 is capable of performing (the test menu capability of each analyzer 104), and the number of slots 207 configured to contain reagent packs or containers for each analyzer 104. Other information regarding the analyzers 104 may additionally or alternatively be included in the inventory data. The requested tests may include requests for testing samples provided to diagnostic laboratory system 100 for one or more of the above-listed tests, for example. Other types of tests may be requested, provided that at least one analyzer is capable of performing that test type. The preferences or priorities (objectives) may include at least one of: load balancing across the analyzers 104, such as providing substantially equal workload on each analyzer 104, minimizing reagent usage at the analyzers 104, reducing turn-around-time (TAT) for tests conducted, reducing quality assurance (QA) costs, or improving system robustness.

As shown in FIG. 3, these preferences/priorities (objectives) may be weighted, wherein an arrow shown to the right side of a particular preference/priority (objective) indicates a greater importance, while an arrow shown to the left side of a particular preference/priority (objective) indicates a lesser importance. For example, arrow 325 indicates that load balancing is of relative great importance, while arrow 327 indicates that quality assurance costs are of less relative importance, in the determination of a particular load plan for diagnostic laboratory system 100. Other information regarding the operation of diagnostic laboratory system 100 and/or the requested tests to be performed may additionally or alternatively be included in input data 326.

Load plan 128 generated by computer server 112 includes computer-executable instructions that may be executed by the system controller 102 such that each of the requested tests is performed on one or more analyzers 104 in the diagnostic laboratory system 100 in accordance with the objectives (preferences/priorities) received in the input data 126 (e.g., input data 326). More particularly, load plan 128 includes computer-executable instructions configured to cause system controller 102 to assign each of the requested test types to be performed at one or more selected analyzers (e.g., analyzers 1041 through 104N) of diagnostic laboratory system 100 in accordance with the objectives (preferences/priorities) received in the input data 126 (e.g., input date 326). Load plan 128 may indicate for each selected analyzer (1041 through 104N), a selected one or more types of tests to be performed thereon.

For example, load plan 128 may provide an assignment of all requested test types to at least a selected sub-plurality of the analyzers 104 such that each selected analyzer 104 has a substantially equal number of requested tests to be performed thereat. That is, in some embodiments, no selected analyzer 104 is assigned, e.g., more than 5%-10% as many tests as a selected analyzer 104 with the least number of assigned tests. This is an example of providing system robustness wherein the analyzers from the non-assigned subgroup are available for use if another analyzer 104 has maintenance scheduled during the planning period, and a further example of load balancing.

In another example, load plan 128 may provide an assignment of all requested test types to at least a selected sub-plurality of the analyzers 104 such that no selected analyzer 104 is given a number of tests to perform that require more than 5%-10% as much time to complete as a selected analyzer that first completes all its assigned tests. This is an example of load balancing.

In still another example, load plan 128 may provide an assignment of all requested test types to at least a selected sub-plurality of the analyzers such that each requested test, or each high-priority test identified in the input data 126 or 326, is completed within a requested time frame (e.g., 24 hours) or by a specified due date and/or time.

In yet another example, load plan 128 may provide an assignment of all requested test types to at least a selected sub-plurality of analyzers such that each selected analyzer has sufficient reagent to perform all requested tests assigned thereto.

The optimization-based load planning module 115 may automatically cause computer server 112 via communication interface 118 to transmit the load plan 128 to the system controller 102. Optionally, a particular respective analyzer 104 having a sample arrive thereat may query the computer server 112 for the type and number of tests to be conducted on the sample at that particular analyzer 104.

Load plan 128 may also or alternatively be viewed and, in some embodiments, edited at user interface 120, and then transmitted to system controller 102 by a human operator. User interface 120 is configured to facilitate interactions between a human operator and the optimization-based load planning module 115. In particular, input devices 122K, 122M and display device 124 may be operative to display a menu including icons, scroll bars, boxes, and/or buttons through which the human operator may interface with the optimization-based load planning module 115 to, e.g., enter input data 126 or 326, view a variety of control and status display screens, and/or view, edit, and/or forward the load plan 128 to the system controller 102. In some embodiments, the control and status display screens may display and enable control of some or all aspects of the optimization-based load planning module 115.

The method assumes that each analyzer 104 has a reagent carousel 205 (or other reagent holding apparatus) that can be loaded with desired reagent packs or the like and the number of slots 207 in these carousels 205 can differ across the analyzers 104. The workload of the laboratory system 100 detailing the samples with time stamps and requested tests on each sample is also assumed to be available. We will refer to this as the payload input (or payload) of the diagnostic laboratory system 100. This payload can also be configured to set the time-window of the samples to be considered in the optimization method such that given a day's (planning period) load of samples. The payload for the planning period can be estimated and provided from an equivalent time period (e.g., shift, day, and week) from a past substantially equivalent time period that may be stored in historical database 114H. For example, it might be desirable to include a payload input of samples that fall within a shift window or up to a certain number of samples for the planning period. Optionally, the payload input could come directly from the LIS 130 for a particular planning period.

In some embodiments, the optimization-based load planning module 115 may be implemented using mixed integer linear programming (MILP). As described above, the optimization-based load planning module 115 receives input data 126 or 326. Input data 126 or 326 may include, additionally or alternatively to the types of input data described above, a time window of the samples to be considered by the optimization-based load planning module 115 (a planning period). In some embodiments, a presumption of the optimization-based load planning module 115 is that a slot 207 (FIG. 2) once loaded with a reagent pack is not reloaded during the optimization time window (during the planning period). Thus, the maximum number of tests that can be run on an analyzer 104 may depend on the number of initial reagent packs, their volumes, and per unit volume consumed by each corresponding ordered test. This input data 126 or 326 may be included in the inventory data for analyzers 104. The optimization-based load planning module 115 may be configured to create an assignment of requested test types based on the payload input (workload), available reagents for the analyzers 104, the number of slots 207, and one or more of the following five user-selected objectives (each of which may optionally be weighted relative to the others by the user): 1) load balancing, 2) efficient reagent usage, 3) reduced turn-around-time (TAT), 4) reduced QA costs, and/or 5) improved system robustness.

Workload of the diagnostic laboratory system 100 detailing the samples and requested tests on each sample is also assumed to be available either as an input from the LIS 130 or optionally can be predicted based on a subset of a larger payload available from historical data, such that the optimization method considers only a limited time frame (planning period).

In some embodiments, the following algorithm may be used to implement the optimization-based load planning module 115 (note that the terms "analyzer," "instrument," and "machine" are used interchangeably herein; and that the terms "slot", "reagent slot" and "wedge" are used interchangeably). The goal of the method implemented by the optimization-based load planning module 115 is then to find an assignment of particular reagents to the slots 207 of each analyzer 104 while optimizing for one or more objectives described herein and subject to certain constraints.

Let $x_{ij}$ denote a binary decision variable, which indicates the assignment of test $j \in \mathcal{T}$ to analyzer $i \in \mathcal{M}$, where $\mathcal{T}$ and $\mathcal{M}$ represent the sets of tests and analyzers, respectively:

$$x_{ij} = \begin{cases} 1, & \text{if instrument } i \text{ has test } j \text{ loaded,} \\ 0, & \text{otherwise.} \end{cases}$$

The notation $$S \in \{0, 1\}^{|\mathcal{A}| \times |\mathcal{T}|}$$

is defined as a binary matrix encoding the required tests for each sample:

$$S_{aj} = \begin{cases} 1, & \text{if sample } a \text{ requires test } j, \\ 0, & \text{otherwise.} \end{cases}$$

where $a \in \mathcal{A}$, $j \in \mathcal{T}$, and $\mathcal{A}$ is the set of all samples.

Given the sample data S, an optimal load plan corresponds to solving a mixed integer program that optimizes the objectives under analyzer and testing related constraints:

$$\begin{aligned} \text{minimize} \quad & f(x_{ij}) \\ \text{subject to} \quad & g(x_{ij}, S) \geq 0, \\ & x_{ij} \in \{0, 1\}, \end{aligned}$$

where f and g are composite functions of objectives and constraints respectively. Table 1 below lists all related variables for quick reference.

TABLE 1

| Variable list involved in the optimization method | | |
|---|---|---|
| Variable Name | Definition | Type |
| $x_{ij}$ | 1 if analyzer i is configured to perform test j | Payload |
| $n_{ij}$ | Total number of test j that will be processed on analyzer i | Optimization |
| $\epsilon_j$ | Slack variable indicating the total number of uncompleted test j due to unmet capacity | Optimization |
| $I_{ai}$ | 1 if analyzer i can be used to cover a test or tests requested for sample a | Optimization |
| $q_j$ | Unified quality assurance related costs of test j | Payload |
| $m_j$ | Minimum number of analyzers to perform test j on | Payload |
| $RE_j$ | Redundancy factor of test j indicating the relative need to run it on multiple analyzers | Payload |

TABLE 1-continued

| Variable Name | Definition | Type |
|---|---|---|
| | Variable list involved in the optimization method | |
| $S_{aj}$ | 1 if sample a requires test j | Payload |
| $w_i$ | Number of slots available on analyzer i | Payload |
| $t_j$ | Amount of time it takes to perform test j | Payload |
| $M_i$ | Maximum throughput of analyzer i in the optimization window (planning period) | Payload |

Optimization Objectives

In some embodiments, the objectives to be optimized may include: quality assurance (QA) cost, test assignment redundancy for system robustness across instruments, and a total number of analyzer visits that samples have to make to complete the required tests in the planning period. An indicator function can be defined as:

$$ I : \mathbb{Z}_+^{N \times J} \to \{0, 1\}^{N \times J}. $$

Here $\mathbb{Z}_+$ refers to the set of all non-negative integers. For any matrix:

$$ M \in \mathbb{Z}_+^{N \times J}, I(M_{ij}) = 1 \text{ if } M_{ij} > 0 \text{ and } I(M_{ij}) = 0 \text{ otherwise.} $$

The mathematical formulations of the optimization objectives are given in more detail below:

1) Quality Assurance (QA) Costs—An objective function to minimize the quality assurance (QA) costs is as follows:

$$ C_{QA} = \sum_{i \in M} \sum_{j \in \mathcal{T}} q_j I(x_{ij}), $$

where $q_j$ is the unified cost of QA material cost, reagent cost, and costs associated with downtime. For each analyzer, the QA cost increases as the analyzer loads more different test types.

2) Unmet Capacity Costs—An objective function to minimize the unmet capacity cost: Given the payload and amount of resources such as the maximum throughput of the analyzers (in the case of CRM) or loaded reagent volume (for SRM) might not suffice to process all the samples, the method denotes the number of uncompleted tests of assay j as $\epsilon_j$ and then state the unmet capacity cost as follows:

$$ C_{MC} = \sum_{j \in \mathcal{T}} \epsilon_j $$

3) Test Assignment Redundancy—An objective function to maximize test assignment redundancy for system robustness. Consider the scenario where it is preferable to perform particular test/tests on several machines for robustness. We assume that a redundancy factor $RE_j > 0$ is provided, for example, within the payload structure. Then the objective function measures the total redundancy achieved by the test assignment:

$$ C_R = \sum_{j \in \mathcal{T}} RE_j \sum_{i \in M} \mathcal{J}(x_{ij}). $$

Maximizing this objective will encourage tests with large redundancy factors to be assigned to more than one analyzer.

4) Workload Balancing—An objective function to minimize for workload balancing. Improving the workload balance of analyzers can reduce excess wear and improve turn around time (TAT) as the bottlenecks are potentially eliminated. The method can explicitly model load balancing through a cost function that can incorporate three different strategies. Each of these balancing strategies has its own merit and the method's framework allows the use of any combination or subset of these strategies, namely: Operation-time based, assay-type based, and/or total-workload based balancing.

4A) Operation-time based balancing-Operation-time based balancing can be achieved through incorporating a cost function that penalizes deviation from a nominal processing time t:

$$ C_{LB,T} = \sum_{i \in M} \left( \bar{t} - \sum_{j \in \mathcal{T}} t_j n_{ij} \right)^2. $$

This average processing time is defined as follows:

$$ \bar{t} = \frac{\sum_{j \in \mathcal{T}} t_j \sum_{a \in \mathcal{A}} S_{aj}}{|M|}, $$

where $t_j$ is the time it takes to perform one sample of assay j.

4B) Assay-type based workload balancing Similarly, in assay-type based workload balancing, the method can use the following cost function:

$$ C_{LB,A} = \sum_{i \in M} \sum_{j \in \mathcal{T}} \left( n_j^{avg} - n_{ij} \right)^2, $$

where the method penalizes the deviation of $n_{ij}$ from a nominal value. This nominal value is chosen to be the following average:

$$ n_j^{\hat{avg}} = \frac{\sum_{a \in \mathcal{A}} S_{aj}}{N_j}, $$

where $N_j$ is the number of analyzers that has test j enabled on its test menu.

4C) Total-workload based balancing—Total-workload based balancing is also enforced by minimizing the deviation from a nominal value:

$$ C_{LB,S} = \sum_{i \in M} \left( n^{avg} - \sum_{j \in \mathcal{T}} n_{ij} \right)^2, \text{ where} $$

$$ n^{avg} = \frac{\sum_{a \in \mathcal{A}} \sum_{j \in \mathcal{T}} S_{aj}}{|M|}. $$

In balancing sample workload, we force the number of samples to be loaded on analyzers to be close to uniformly distributed, by penalizing the deviation of number of samples loaded on each analyzer from a theoretical average. The objective function can be written as follows, $$C_{LB,SL} = \sum_{i \in M} \left( \sum_{a \in \mathcal{A}} I_{ai} - \frac{|\mathcal{A}|}{|M|} \right)^2$$

where $\mathcal{I}_{ai}$ is a binary variable indicating whether sample a will require instrument i:

$$J_{ai} = \begin{cases} 1 & \text{if sample } a \text{ requires instrument } i \\ 0 & \text{otherwise.} \end{cases}$$

$|\mathcal{A}|$ and $|\mathcal{M}|$ are the size of the set A and M, corresponding to the total number of samples and total number of analyzers accordingly. Minimizing this objective function will encourage each analyzer to analyze a similar amount of samples.

Then the overall load balancing objective can be written as follows:

$$C_{LB} = \beta_1 C_{LB,T} + \beta_2 C_{LB,A} + \beta_3 C_{LB,S} + \beta_4 C_{LB,SL},$$

where $\beta_1$, $\beta_2$, $\beta_3$ and $\beta_4$ are non-negative weights adjusting the relative contribution of each balancing strategy.

To avoid the computational burden stemming from the use of quadratic objectives, the method minimizes the linear deviation from the nominal values through the use of integer non-negative slack variables for all three cost functions that make up $C_{LB}$. In linearizing $C_{LB,A}$ the method uses $$n_+^{ij}$$

and $$n_-^{ij}$$

as slack variables corresponding to the excess and missing load of test j on instrument i:

$$\sum_{i \in M} \sum_{j \in \mathcal{T}} \left( n_-^{ij} + n_+^{ij} \right)$$

subject to $n_{ij} = n_{avg}^j + n_+^{ij} - n_-^{ij}$, $n_+^{ij} \ge 0, n_-^{ij} \ge 0.$ Linearization of $C_{LB,T}$, $C_{LB,S}$ and $C_{LB,SL}$ follows a very similar approach with the introduction of slack variables and is left out for conciseness.

5) Total Analyzer Visits—This is an objective function that seeks to minimize the total analyzer visits to be made by the samples. To minimize the number of stops a sample makes the method minimizes the following cost function:

$$C_{stops} = \sum_{a \in \mathcal{A}} \sum_{i \in M} J_{ai},$$

where $\mathcal{I}_{ai}$ is the same binary variable indicating whether sample $\alpha$ will require instrument i, defined in the constraint 4 below.

Minimizing this objective will encourage sample a to request as few analyzers as possible, and thus reduces the number of stops it makes, directly optimizing TAT.

Optimization Constraints

In this subsection, we provide the mathematical formulation of the optimization constraints. According to the method, the formulation of each optimization constraint can be as follows:

1. Number of reagent packs to load can not be greater than the number slots in the analyzer:

$$0 \le \sum_{j \in \mathcal{T}} x_{ij} \le w_i, \forall\, i \in M.$$

2. The types of loaded reagent should cover all the requested tests for the samples: This constraint ensures that for each requested test, there is at least one analyzer to perform it:

$$J \left( \sum_{a \in \mathcal{A}} S_{aj} \right) \le J \left( \sum_{i \in M} x_{ij} \right), \forall\, j \in \mathcal{T}.$$

3. All requested tests should be completed within the considered optimization window (planning period). This constraint is directly related to the objective function, the unmet capacity $C_{MC}$ defined above and ensures that tests are completed as much as possible. The method can account for the possibility of uncompleted samples due to capacity or time-frame issues by using the slack variable $\epsilon_j$ for each test j. The constraint then becomes:

$$\sum_{i \in M} n_{ij} + \epsilon_j \ge \sum_{a \in \mathcal{A}} S_{aj}, \forall\, j \in \mathcal{T}, \text{ with}$$

$$n_{ij} \ge 0, \forall\, i \in M, j \in \mathcal{T},$$

$$\epsilon_j \ge 0.$$

4. Analyzer i is not allowed to run test j if that test is not enabled (or does not exist in the test menu):

$$\begin{cases} n_{ij} \ge 0, & \text{if instrument } i \text{ is configured/allowed to run test } j, \\ n_{ij} = 0 \text{ and } x_{ij} = 0, & \text{otherwise.} \end{cases}$$

5. Volume capacity constraint: The number of tests to be performed by an analyzer within the optimization window (planning period) cannot be larger than its total maximum throughput:

$$\sum_j n_{ij} \le M_i, \forall\, i \in M.$$

wherein $M_i$ is the maximum throughput of the analyzer i during current time shift.

6. Redundancy constraints on favorable tests: This constraint compliments the objective function maximizing the total redundancy factor described above by explicitly enforcing a minimum number of analyzers, $m_j$, running test j:

$$\sum_{i \in M} \mathcal{J}(x_{ij}) \ge m_j, \forall\, j \in \mathcal{T}.$$

7. Number of stops related constraints: In minimizing the number of total stops made by all the samples as given in objective, we need to enforce that there is at least one set of analyzers to perform the tests required. We denote the set of tests requested by sample a by:

$$\mathcal{R}_a = \{j | S_{aj} > 0, j \in \mathcal{T}\}$$

and the set of analyzers that hav test j assigned by:

$$\mathcal{K}_j = \{i | \mathcal{T}(x_{ij}) > 0, i \in \mathcal{M}\}.$$

Then the cover constraint can be written as follows:

$$\sum_{j \in \mathcal{R}_a} \sum_{i \in \mathcal{K}_j} \mathcal{T}_{ai} \geq 1, \forall a \in \mathcal{A}.$$

It should be noted that the term $$\sum_{i \in \mathcal{K}_j} \mathcal{T}_{ai}$$

is a non-linear combination (multiplication) of two indicator variables, $\mathcal{T}(x_{ij})$ and $\mathcal{T}_{ai}$, that are both tied to the optimization variables $x_{ij}$. This non-linearity imposes additional computational complexity. To alleviate this, according to the method, this combination is relaxed by introducing an additional binary slack variable $II_{aij}$ and transform the original constraint into following:

$$\sum_{j \in \mathcal{R}_a} \sum_{i \in \mathcal{M}} II_{aij} \geq 1, \forall a \in \mathcal{A},$$

subject to $II_{aij} \leq \mathcal{T}(x_{ij})$, $II_{aij} \leq \mathcal{T}_{ai}$, $II_{aij} \geq \mathcal{T}(x_{ij}) + \mathcal{T}_{ai} - 1.$ The resulting optimization problem is an instance of mixed integer linear programming and can be solved with various techniques such as branch and bound. Multi-objective optimization can be handled with lexicographic or weighted optimization.

Figures 4A, 4B, 4C:
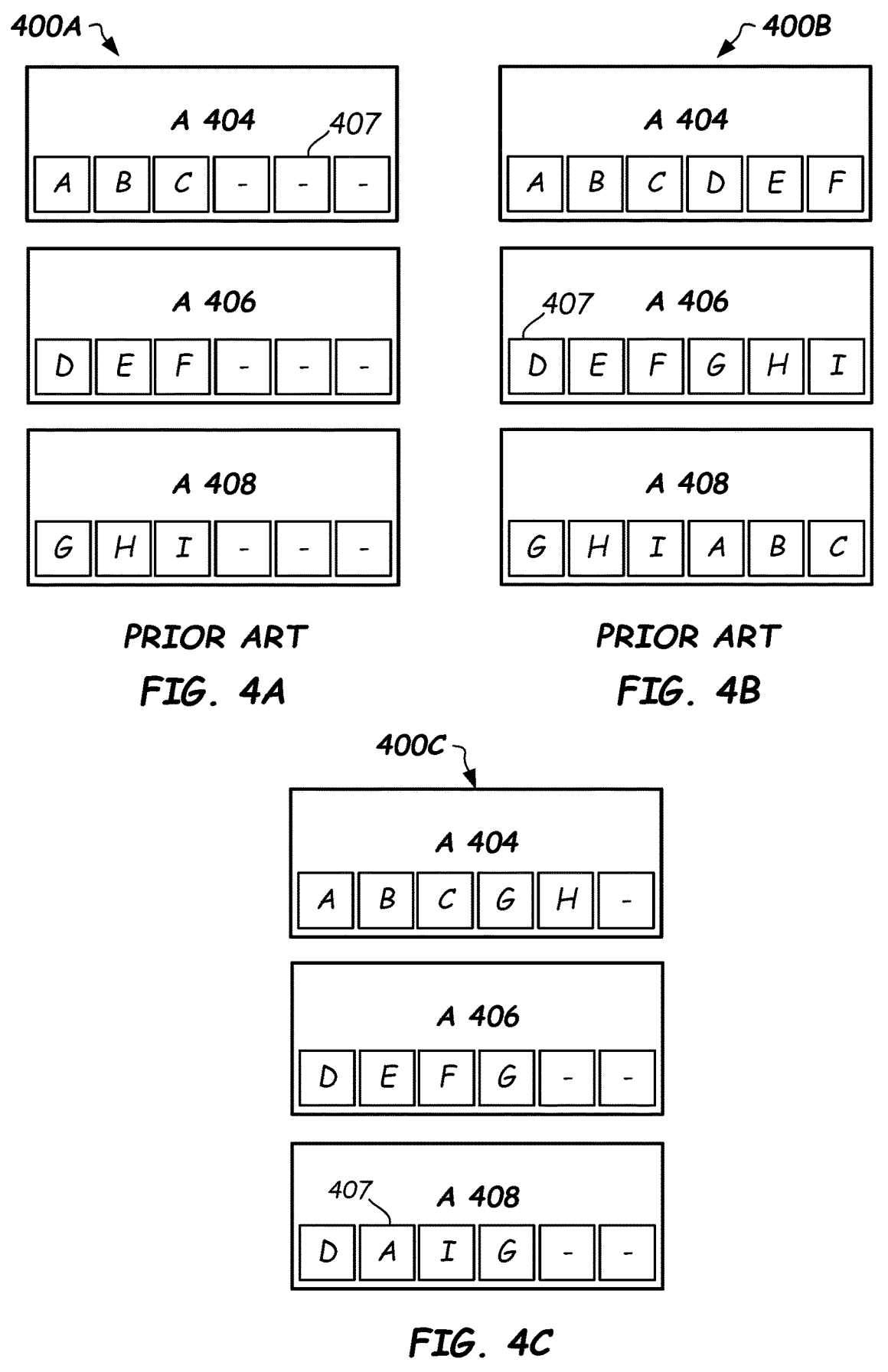

FIGS. 4A and 4B illustrate examples of load plans 400A and 400B that may be created for analyzers 404-408 conventionally, while FIG. 4C illustrates an example of a load plan 400C that may be created for analyzers 404-408 by the standard optimization-based load planning module 115 according to one or more embodiments. Each of the load plans 400A, 400B, and 400C are based on the same set of objectives and constraints for a diagnostic laboratory system 100 offering a menu of nine types of immunoassay tests: A, B, C, D, E, F, G, H, and I, wherein tests A and G are frequently requested together. The example diagnostic laboratory system 100 has three analyzers A 404, A 406, and A 408, each having six reagent slots 407 (only one labeled in each of FIGS. 4A-4C). Each of the reagent slots 407 may be loaded with a particular reagent pack to be used for one of the nine types of tests. The objectives can be selected to be load balancing, reagent usage, quality assurance costs, and system robustness (e.g., sufficient redundancy to overcome an analyzer 104 failure).

As shown in FIG. 4A, conventional load plan 400A may evenly distribute the nine tests across the three analyzers A 404, A 406, and A 408, such that each performs a different set of three tests: analyzer 404 A performs tests A, B, and C; analyzer A 406 performs tests D, E, and F; and analyzer A 408 performs tests G, H, and I. A problem may result, however, if any one of analyzers A 404, A 406, and/or A 408 fails. The tests assigned to the failed analyzer cannot be performed at either of the other two operating analyzers, as load plan 400A has no redundancy. Furthermore, any sample requiring tests A and G has to visit both analyzers A 404 and A 408, which may degrade system throughput and turn-around-time (TAT).

FIG. 4B shows conventional load plan 400B, which is based on redundancy. Each analyzer A 404, A 406, and A 408 performs a different combination of six tests: analyzer A 404 performs tests A, B, C, D, E, and F; analyzer A 406 performs tests D, E, F, G, H, and I; and analyzer A 408 performs tests G, H, I, A, B, and C. However, load plan 400B results in double the reagent costs, as each test is performed in two analyzers, and twice the quality assurance costs, as each analyzer (performing six types of tests) requires twice as much calibration and quality control as load plan 400A (wherein each analyzer performs only three types of tests).

FIG. 4C shows load plan 400C created by the standard optimization-based load planning module 115 according to embodiments. Load plan 400C distributes the testing across analyzers A 404, A 406, and A 408 such that each analyzer performs only five or four tests, thus achieving load balance and reducing quality assurance costs. That is, analyzer A 404 performs tests A, B, C, G, and H; analyzer A 406 performs tests D, E, F, and G; and analyzer A 408 performs tests D, A, I, and G. Moreover, tests A and G, commonly requested together, are both performed at two of the three analyzers (laboratory analyzers A 404 and A 408), thus reducing the number of visits to analyzers per sample, which in turn may increase throughput and/or TAT. Downtime exposure due to analyzer failure is also reduced because three of the nine types of tests (A, D, and G) are performed in at least two of the three analyzers. And load plan 400C results in lower reagent costs as all slots 407 are not used (and loaded with reagent packs).

FIG. 5 illustrates a flowchart of the standard method 500 of optimization-based load planning for a diagnostic laboratory system 100 according to one or more embodiments of the disclosure. Standard method 500 may be carried out by a suitable computer server, such as, e.g., computer server 112, a suitable system controller, such as, e.g., system controller 102, or other suitable computing device. Standard method 500 may include, at process block 502, receiving, at a computer server, computer-readable data comprising an inventory of a plurality of analyzers 104 included in a diagnostic laboratory system 100, types and numbers of requested tests to be performed by the diagnostic laboratory system 100, and preferences or priorities (objectives) related to operation of the diagnostic laboratory system 100 and to the types and numbers of requested tests to be performed. For example, the computer-readable data may represent input data 126 of FIG. 1 input from user interface 120 or input data 326 of FIG. 3.

Standard method 500 may also include, in process block 504, determining, via an optimization-based load planning module executing on the computer server 112, a load plan 128 for performing each of the requested test types in the diagnostic laboratory system 100. The load plan may comprise computer-executable instructions configured to cause a system controller 102 of the diagnostic laboratory system 100 to assign and direct each of the requested test types to be performed at one or more selected analyzers of the diagnostic laboratory system 100 in accordance with the one or more of the preferences or priorities.

In some embodiments, the load plan 128 may include computer-executable instructions indicating assignment of all requested test types to at least some selected analyzers 104 such that each selected analyzer 104 has a substantially equal number of requested tests to be performed to accomplish load balancing. In other embodiments, the load plan 128 may include computer-executable instructions indicating assignment of all requested tests to at least some selected analyzers 104 such that each selected analyzer has sufficient reagent to perform all requested tests assigned thereto to accomplish efficient reagent use.

In one or more embodiments, standard method 500 may further include transmitting the load plan 128 from the computer server 112 to the system controller 102 of the diagnostic laboratory system 100, wherein the load plan 128 is executed by the system controller 102 to assign each of the requested test types to be performed at one or more selected analyzers 104 of the diagnostic laboratory system 100 in accordance with one or more of the preferences or priorities (objective functions) as bound by the constraints.

Large Scale Data Techniques for Laboratory Data Processing and Optimization

In this section, a computationally-efficient load plan optimization method 700 in accordance with the disclosure is described. The computationally-efficient load plan optimization method 700 enables the processing of extremely large amounts of data from such large-scale diagnostic laboratory systems 100. The large-scale diagnostic laboratory systems 100 may automatically process exceedingly large numbers of biological samples, such as greater than about 10,000 samples per day, and do so in a computationally-efficient manner. In particular, the method 700 implements a data-reduction scheme in order to effectively deal with the large amount of laboratory data to be processed to generate the load plan. In particular, the method 700 implements a data-reduction scheme to reduce a number of variables that are created.

The data-reduction schemes can include: 1) solving successive surrogate problems, 2) representing common test order patterns so that common collections (groups) of samples can be represented by meta-samples, 3) by iteratively optimizing over successive time periods, or 4) any combination of the aforementioned 1-3.

Figure 6:
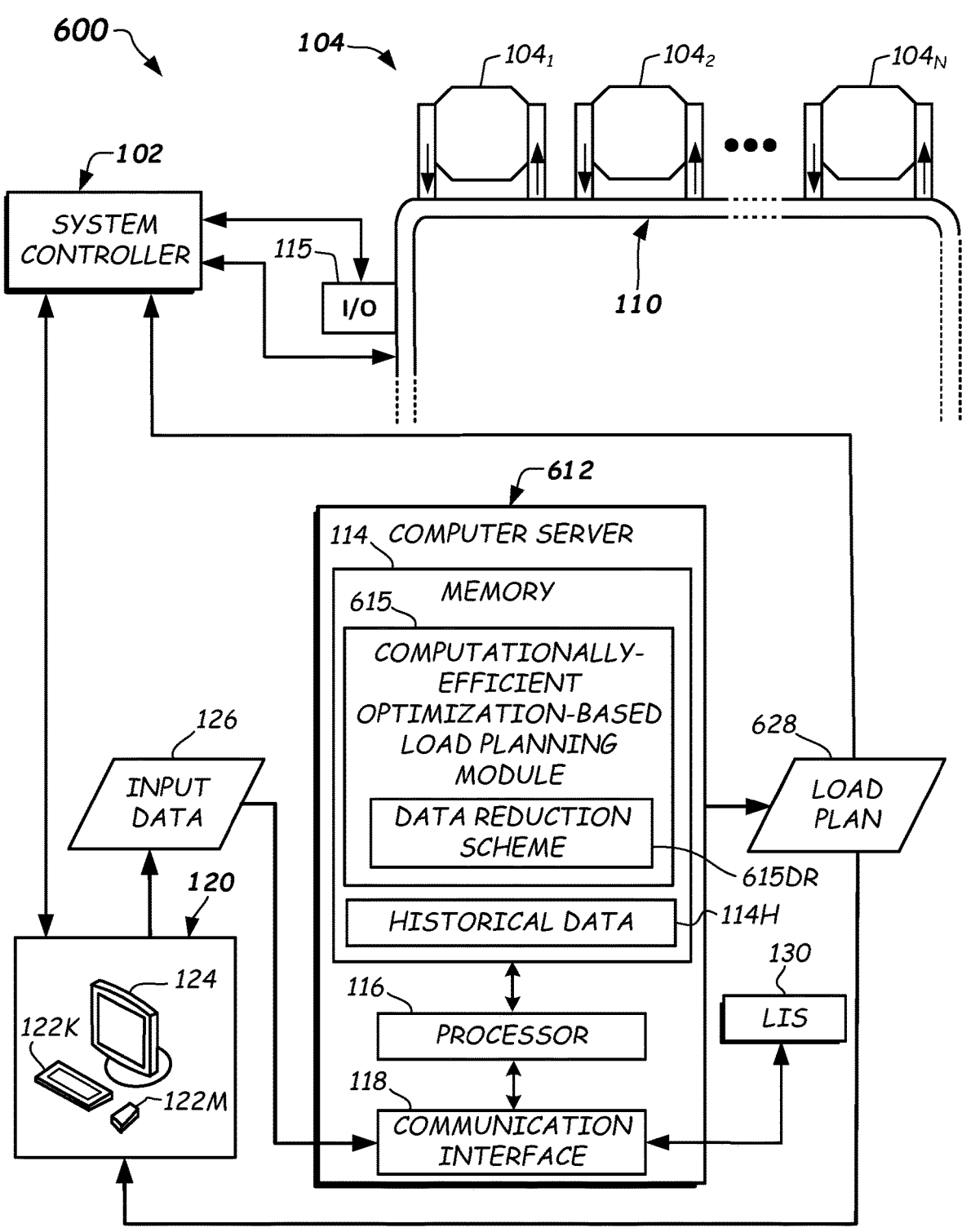
FIG. 6 illustrates a schematic block diagram of a diagnostic laboratory system including a computationally-efficient optimization-based load planning module including a data-reduction scheme according to one or more embodiments.

In more detail, a computationally-efficient optimization method 700 for optimization-based load planning for a diagnostic laboratory system 600 according to one or more embodiments of the disclosure is best shown in FIGS. 6 and 7. The diagnostic laboratory system 600 of FIG. 6 is functionally the same as FIG. 1, except that the memory 115 of the computer server 612 contains a computationally-efficient optimization-based load planning module 615.

In more detail, the method 700 includes, in block 702, receiving, at a computer server (e.g., computer server 612), computer-readable data concerning analyzers 104 included in a diagnostic laboratory system (e.g., diagnostic laboratory system 600), types and numbers of requested tests to be performed by the diagnostic laboratory system, and preferences or priorities related to operation of the diagnostic laboratory system and to the types and numbers of requested tests to be performed (the payload). For example, the computer-readable data may represent input data 126 of FIG. 1 input from user interface 120 or input data 326 of FIG. 3

Computationally-efficient optimization load planning method 700 may also include, in block 704, determining, via a computationally-efficient optimization-based load planning module executing on the computer server 712, a load plan 128 for performing each of the requested test types over a planning period. The planning period may be a period of time or a period over which a predetermined number of requested tests (or samples) are to be processed. For example, the number and type of requested tests can come from a laboratory information system (LIS) 130, or can be provided as input from historical data over a period of time in the past substantially equivalent to the current planning period that will operate as a good estimate of the number and types of tests that can be expected over the current planning period. For example, the historical data may be from a like day (e.g., last Tuesday) from a previous week and the current planning period is an upcoming Tuesday. The determined load plan may comprise computer-executable instructions configured to cause a system controller (e.g., system controller 102) to assign each of the requested test types to be performed at one or more selected analyzers (e.g., analyzers 104) in accordance with the one or more of the preferences or priorities (objectives) and further subject to constraints. Furthermore, the computationally-efficient optimization-based load planning module 615 is considered computationally-efficient by implementing a data-reduction scheme 615DR. The system controller 102 may also direct each of the requested tests to be performed based on any suitable logical rules.

Each example data-reduction scheme 615DR will now be described in detail with reference to FIGS. 8-10 herein.

Processing Surrogate Problems

In optimizing and processing large-scale data, if the number of variables used by the optimization method for generating the load plan 128 scales up fast with respect to patient samples or a number of tests ordered, then this can render the optimization method unusable, in that the processing time may be exceeding long (e.g., weeks). Considering that new optimized load plans may need to be generated every shift or every day, this extended computation time is simply untenable. In extreme cases, the number of variables to be created might be more than what today's supercomputers are capable of effectively processing, in that there is not enough memory to store the billions of variables created. In dealing with such large computational burden, the method 800, in a first embodiment, uses a surrogate version of the original standard optimization method 500 that is computationally easier to solve. Although there might be a slight degradation in the performance, it may potentially still benefit the operation of such a large-scale diagnostic laboratory system 600 by reducing the number of variables and length of time needed to process the optimization problem.

In a first example, as shown in FIG. 8, the optimization method 800 is accomplished using a surrogate. The surrogate is illustrated through using the standard optimization method described above and showing that the run-time can be significantly reduced using the surrogate optimization approach. In the standard optimization method 500, the optimization variables that are created are either binary values or integer values (See Table 1) and hence the resulting problem is an instance of an integer optimization. In such standard optimization methods 500, the number of binary and integer variables directly affects the solution time. The greater number of binary and integer optimization variables, the longer the solution time will be. In particular, in the standard optimization methods, $x_{ij}$, $n_{ij}$, $\in_j$, $I_{ai}$, and $II_{aij}$ are created as binary or integer values. Although the number of variables created due to $x_{ij}$, $n_{ij}$ and $\in_j$ is not necessarily significant for computation, the number of stops related variables $I_{ai}$ and $II_{aij}$ can be in the order of millions depending on the daily workload (number of tests) and setup of the diagnostic laboratory system 600 (number of analyzers and number of assays to be performed). The method 800 utilizes a relaxation to the original standard optimization method variables as listed in Table 1 above. The method 800 using the surrogate optimization approach as the data-reduction scheme 615DR can be identical to standard optimization method 500 in terms of objectives and constraints except for the type of variables it uses. As the number of binary and integer valued variables is greatly reduced, method 800 can be orders of magnitude computationally faster than the standard optimization method 500, especially when large-scale data is present. The surrogate optimization method 800 reduces the number of binary and integer valued variables by providing a two-phase optimization approach, namely including phase I and phase II to be described below. As the surrogate problem is faster and it returns the assignments of tests, it is possible that due to relaxed variables, samples will be fractionally assigned such that $n_{ij}$ is not integer or $I_{ai}$ will not be binary.

According to the method 800, in block 802, the sample data and corresponding test order data are assembled to provide the payload for the optimization problem. In the first phase (Phase I) of the method 800, in block 804, the method 800 removes integer and binary constraints from all but assay assignment variable $x_{ij}$. The method 800 then, in block 806, solves the optimization problem to result in $x_{ij}$ and non-binary $I_{ai}$ and $II_{aij}$.

The method 800, in a second phase (Phase-II), solves for binary valued $I_{ai}$ so that rounding of $n_{ij}$ can be anchored to the binary optimized $I_{ai}$. In particular, the method 800 builds the optimization solution such that if a test (assay) is assigned to an analyzer 104, it cannot be removed and only new tests (assays) can be assigned to the analyzers 104. This is achieved by keeping $x_{ij}$ fixed and defining and optimizing over the following slack variable:

$$\text{slack\_x}_{ij} = \begin{cases} 1 & \text{if instrument } i \text{ has test } j \text{ added} \\ 0 & \text{otherwise.} \end{cases}$$

The method 800 then enforces the following constraint to make sure that there is no double assignment of the same test to any analyzer 104:

$$\text{slack\_x}_{ij} \leq 1 \ \forall \, i \in \mathcal{M}, j \in \mathcal{J}.$$

Then the final assignment of assays is given by:

$$\bar{x}_{ij} = \text{slack\_x}_{ij} + x_{ij} \ \forall \, i \in \mathcal{M}, j \in \mathcal{J}.$$

Thus, method 800 in Phase II, in block 808, starts with $x_{ij}$ and add small amounts of new assays to analyzers 104 until $I_{ai}$ and $II_{aij}$ are binary. The method 800 can optimize for load balancing, number of stops, and/or marginal quality assurance costs (due to possible addition of new tests). The expressions for the load balancing cost function and the number of stops cost function are same as before, as they are over $n_{ij}$ and $I_{ai}$. The marginal quality assurance cost is now over slack\_$x_{ij}$ and can be incorporated as follows:

$$C_{MQA} = \sum_{i \in \mathcal{M}} \sum_{j \in \mathcal{J}} q_j \mathcal{J}(\text{slack\_x}_{ij})$$

The constraints of the method 800, in this example, are due to the test menu, number of stops related constraints, and the aforementioned constraints configured to prevent double assignments. The test menu constraints may be modified to account for the new decision variable as follows:

$$\begin{cases} n_{ij} \geq 0, & \text{if instrument } i \text{ is configured/allowed to run test } j, \\ n_{ij} = 0 \text{ and } x_{ij} + \text{slack\_x}_{ij} = 0, & \text{otherwise.} \end{cases}$$

Similarly number of stops constraints are over $x_{ij}$+ slack\_$x_{ij}$ instead of $x_{ij}$. Once the method 800 is carried out, $\tilde{x}_{ij}$ is the final assignment of tests to analyzers 104 and $n_{ij}$ can be made to be an integer by using $II_{aij}$ as it encodes test processing information. In particular, the optimization problem is solved, in block 810, to generate a load plan 628 with $x_{ij}$, $I_{ai}$ and $II_{aij}$ constrained to be binary. Table 1 above shows the variables for Phase I and Phase II of the surrogate optimization approach as compared to the standard optimization approach.

Grouping of Samples into Meta-Samples

Some large-scale diagnostic laboratory systems 600 receive millions of samples per month. Many of the these samples can have/share the same test order patterns. In one example, assuming that the diagnostic laboratory system 600 conducts four tests $tx_1$, $tx_2$, $tx_3$, and $tx_4$ the sample orders can include any combination of these tests. Continuing with the example, in most cases most of the payload might be dominated by samples that merely order tests such as $tx_1$ and $tx_2$ together, and $tx_1$ and $tx_3$ together, out of the possible 15 combinations. In general in the setting of the diagnostic laboratory system 600, the inventor observed that even when there are hundreds of tests (assays), many samples are identical in their test orders, as the tests ordered are mainly from a small subset of the all possible tests. Many of the tests that the diagnostic laboratory system 600 processes can be classified as "esoteric" as they are not commonly ordered in the work order (payload). In accordance with this observation, the inventor has recognized that the samples with same ordered tests and high incidence in the payload can be grouped and represented in the optimization method 900 by fewer so-called "meta-samples."

Thus sample grouping, used with the optimization method 900 as a data-reduction scheme, creates a meta-sample for each highly-ordered test pattern ordered for the samples. A highly-ordered test pattern can be a test order that repeats itself 10,000 times or more for large diagnostic laboratory systems, and 1,000 or more for small diagnostic laboratory systems during the planning period. The number of meta-samples created for a particular pattern is dependent on a factor referred to herein as the reduction factor $\eta \in (0, 1)$. For each subset of assays, $l \in \mathcal{T}$, the method 900 defines the following:

$$G_l = \left\{ a \in S \mid \sum_{j \in l} S_{aj} = |l|, \sum_{j \in \mathcal{T}} S_{aj} = |l| \right\},$$

where |·| is the cardinality operator. Simply put, $G_l$ indexes the samples that have orders for the tests in the subset l. Given a threshold, th, that can be adjusted based on the available computational resources, each $G_l$ with $|G_l| \geq th$, the method 900 performs a reduction and obtains meta-samples in block 902. In particular we define the surjective mapping as follows:

$$G_l \to \overline{G}_l \text{ where } |\overline{G}_l| = \text{ceil}(\eta * |G_l|),$$

where ceil is the ceiling function that rounds decimal point numbers to the closest integer value that is larger. In block 904, each sample in $G_l$ is then mapped to one of the meta-samples in the set $\overline{G}_l = \{g_{l,1}, g_{l,2}, \ldots, g_{l,|G_l|}\}$. For subsets that have less than th samples, we do not perform any reduction.

This reduction and mapping operation of the method 900 reduces the number of samples to be considered in any downstream application. However the meta-samples and regular samples should not be processed together as they represent a different encoding of samples. The method, in block 904, then splits the meta-samples and regular samples into a major payload and a residual payload. In the major payload, each sample is a meta-sample representing more than one actual sample whereas in the residual payload each sample represents itself.

Having represented the total workload in two different representations, the method 900 implements a divide-and-conquer approach to obtain a load plan of test assignments to the analyzers 104. Since the major payload accounts for the majority of the samples in the workload, the obtained solution may give more preference to optimizing major payload in comparison to the residual payload. With this in mind, the method 900 starts with the major payload and may, in block 908, use any suitable optimization method such as the standard optimization method 500, to obtain a first solution. Load balancing objectives and capacity constraints have to be modified accordingly as each meta-sample represents more than one actual sample. Given the solution due to the major payload, the method then solves a problem very similar to the Phase-II that was described for the surrogate optimization method 800. However, unlike the surrogate method, Phase-II employed above, the payload data changes in the second step. Thus, the method 900 employs the following constraint to prevent the removal of tests from analyzers 104 and only allow the addition of new tests:

$$x\_residual_{ij} + x\_major_{ij} \leq 1 \ \forall \ i \in \mathcal{M}, j \in \mathcal{J},$$

where $x\_major_{ij}$ and $x\_residual_{ij}$ are the solutions to the major and residual payloads, respectively. These constraints make sure that there is fidelity to the solution obtained due to optimizing for the major payload and any addition will be due to the residual payload. Thus, in block 910, the method 900, starting with the assignments $x\_major_{ij}$ obtained from the optimization of the major payload, and without removing any assigned assay types from any analyzer 104, uses an optimization method, such as the optimization method 800 described in FIG. 8, on the residual payload to obtain a final solution.

In some cases, the residual payload might still result in a large-scale problem that may not be amenable to processing or optimization due to computational challenges. In such cases one or more additional rounds of reduction can be applied on the residual payload resulting in its own major and residual payloads until the resulting optimization problems are computationally efficient.

Iterative Optimization of Time-Dependent Data

The time-dependent nature of diagnostic laboratory data can enable special processing and optimization. In particular, if the provided data spans a planning period that can exhibit seasonality (i.e., changing over various seasons) such as shift-based, daily, weekly, monthly, quarterly or yearly, a representative portion of data can be used in an initial optimization. The remaining data can then be added iteratively thus building on the existing processing optimization results. Here our assumption is that the time series data generated by workload of a diagnostic laboratory system 600 is composed of seasonal, growth, and random components and between seasonal data chunks the difference is mainly be due to growth and random components. Given this intuition, we expect that the processing or optimization results of seasonal chunks should be similar with minor differences due to random variations and growth (positive or negative) in the business. Thus, in another embodiment, referred to herein as "iterative optimization method" 1000, the method 1000 involves iterative processing of such time-dependent data. This iterative optimization method 1000 can significantly reduce the amount of data that the processing and optimization methods have to handle at a time.

The iterative optimization method 1000 is illustrated in FIG. 10 and can be implemented through the iterative use of the standard optimization method 500, for example, with laboratory workload data that spans multiple seasonal chunks. For the example described here, it is assumed that the seasonality is weekly, meaning that there is a weekly pattern in the provided payload data. It should be understood, however, that other seasonality types can be used. Thus, the method 1000, in block 1002, runs a first load plan optimization (e.g., the standard optimization method 500) for a first portion of a planning period to generate a load plan for analyzers 104 in a diagnostic laboratory system 600 for the first portion. The method 1000 refers to the solution of the first week of data $x_{ij,t_1}$. Then for the second week of data, the method 1000, in block 1004, starting with the assignments $x_{ij,t_1}$ obtained from the optimization of the first portion, and without removing any assigned assay types from any analyzer 104, runs a second load plan optimization (e.g., using the standard optimization method 500) for a second portion of the planning period to generate a final load plan for analyzers 104 in the diagnostic analyzer system 600. The optimization method 1000 may use the decision variable $x_{ij,t_2}$. Different than the objectives and constraints used in the solution of $x_{ij,x2}$, the method imposes the following additional constraint:

$$x_{ij,t_2} \geq x_{ij,t_1} \ \forall \ i \in \mathcal{M}, j \in \mathcal{J}.$$

This constraint implies that the method 1000 does not remove any test assignments from any analyzers 104 going from week 1 to 2; but new tests can be added and $n_{ij}$ and other optimization variables can be optimized. Generalizing from week 1 and 2 to any consecutive weeks k and k+1 the continuity constraints can be written as follows:

$$x_{ij,t_{k+1}} \geq x_{ij,t_k} \ \forall \ i \in \mathcal{M}, j \in \mathcal{T}.$$

The end result of the first and second load plan optimizations from block 1002 and 1004 provide a load plan 628 for the planning period. The divide and conquer type of method 1000 presented here is based on the assumption that the data has repeating seasonal patterns with differences in the seasonal chunks are merely due to trend and random noise components. If this is not the case, such that there is no clear pattern in the divided time chunks, then incorporating the continuity constraints would not result in sensible results as the workload is very different from one chunk of data to another.

Combination Strategies

The three proposed data-reduction schemes above can be combined together in different ways to reach computational feasibility. For example, the surrogate method 800 can be applied to any standard optimization problem as it does not make any assumptions about the data. The method 900 of grouping samples to form meta-samples can be applied for many workloads as many samples share common test order profiles. The iterative optimization method 1000 of time dependent data is based on the assumptions that longitudinal data is available and there is seasonality present. For example given data with weekly seasonality, each week's data can be factored into major payload and residual payload and the processing of these payloads can be achieved by solving surrogate method's 800 Phase-I and Phase-II successively. Thus, a combination of all three data-reducing methods 800, 900, 1000 may be used. In a case where iterative optimization method 1000 based on seasonal data chunks is not possible, an optimization method using a combination of grouping of samples of method 900 and a surrogate method 800 having a phased solution can be applied. Any combination of these above-methods can be used based on the specifications of the optimization problem and data at hand.

While the disclosure is susceptible to various modifications and alternative forms, specific method and system embodiments have been shown by way of example in the drawings and are described in detail herein. It should be understood, however, that the particular methods and systems disclosed herein are not intended to limit the disclosure but, to the contrary, to cover all modifications, equivalents, and alternatives falling within the scope of the claims.

What is claimed is:

1. A method of load planning in a diagnostic laboratory system, comprising:

receiving, at a computer server, computer-readable data concerning analyzers included in the diagnostic laboratory system, and test types and test numbers to be performed within the diagnostic laboratory system over a planning period, and preferences or priorities related to operation of the diagnostic laboratory system and to the test types and test numbers of the requested tests to be performed;

creating a number of load planning variables based on the computer readable data via an optimization-based load planning module executing on the computer server;

reducing the number of load planning variables via a data-reduction scheme; and determining, via the optimization-based load planning module that includes the data-reduction scheme executing on the computer server, a load plan for performing each of the requested test types over the planning period, the load plan comprising computer executable instructions configured to cause a system controller to assign each of the requested test types to be performed over the planning period to one or more selected analyzers in accordance with the one or more preferences or priorities.

2. The method of claim 1, wherein the reducing the number of load planning variables via the data-reduction scheme comprises solving successive surrogate problems by, in a first phase, removing integer and binary constraints from most but not all of the load planning variables that are binary values or integer values.

3. The method of claim 1, wherein the reducing the number of load planning variables via the data-reduction scheme comprises representing common test order patterns so that common groups of samples can be represented by meta-samples, wherein each meta-sample represents more than one sample, and the determining comprises determining a load plan first for the meta-samples and then for the remaining samples.

4. The method of claim 1, wherein the reducing the number of load planning variables via the data-reduction scheme comprises iteratively optimizing over successive time periods within the planning period including a first optimization for a first time period within the planning period and then a second optimization for a second successive time period within the planning period that includes the results of the first optimization.

5. The method of claim 1, wherein the data-reduction scheme comprises any combination of: solving successive surrogate problems, representing common test order patterns so that common groups of samples can be represented by meta-samples, and iteratively optimizing over successive time periods within the planning period.

6. The method of claim 1, further comprising transmitting the load plan to the system controller of the diagnostic laboratory system.

7. The method of claim 1, wherein the computer-readable data concerning analyzers comprises:

a number of the analyzers in the diagnostic laboratory system, types of tests on a test menu that each analyzer is capable of performing, a number of tests each analyzer is capable of performing, and a number of reagent slots in each analyzer.

8. The method of claim 1, wherein the preferences or priorities include at least one of: load balancing across the analyzers, reagent usage at the analyzer, reduced turn-around-time, quality assurance costs, and system robustness.

9. The method of claim 1, wherein the load plan comprising computer-executable instructions indicates an assignment of all requested test types to at least some selected analyzers such that each selected analyzer has a substantially equal number of requested tests to be performed thereon.

10. The method of claim 1, wherein the load plan comprising computer-executable instructions indicates an assignment of all requested test types to at least some selected analyzers such that each selected analyzer has sufficient reagent to perform all requested tests assigned thereto.

11. A diagnostic laboratory system, comprising:

a system controller;

a plurality of analyzers connected to each other via one or more automated tracks for transporting sample containers to and from the plurality of analyzers under the control of the system controller, each of the plurality of analyzers configured to perform one or more tests on one or more samples contained in the sample containers over a planning period; and a computer server coupled to the system controller, the computer server comprising an optimization-based load planning module including a data-reduction scheme executing on the computer server, a load plan for performing each of one or more requested test types over the planning period, the load plan comprising computer executable instructions configured to cause a system controller to assign each of the one or more requested test types to be performed over the planning period to one or more selected analyzers in accordance with one or more received preferences or priorities, wherein the optimization-based load planning module including the data-reduction scheme executing on the computer server comprises:

creating a number of load planning variables based on computer readable data concerning analyzers included in the diagnostic laboratory system, and test types and test numbers to be performed within the diagnostic laboratory system over a planning period, and preferences or priorities related to operation of the diagnostic laboratory system and to the test types and test numbers of the requested tests to be performed; and reducing the number of load planning variables by solving successive surrogate problems by, in a first phase, removing integer and binary constraints from most but not all load planning variables that are binary values or integer values.

12. The diagnostic laboratory system of claim 11, wherein the optimization-based load planning module including the data-reduction scheme executing on the computer server further comprises one or both of representing common test order patterns so that common groups of samples can be represented by meta-samples, and iteratively optimizing over successive time periods within the planning period.

13. The diagnostic laboratory system of claim 11, wherein at least some of the analyzers have a reagent carousel containing slots.

14. The diagnostic laboratory system of claim 11, comprising an input/output device configured to input the sample containers onto the automated track.

15. The diagnostic laboratory system of claim 11, comprising an inventory of the plurality of analyzers that indicates a number of laboratory analyzers, types of tests each analyzer is capable of performing, and a number of reagent slots for each analyzer.

16. The diagnostic laboratory system of claim 11, wherein the preferences or priorities include at least one of: load balancing across the analyzers, reagent usage at the analyzer, reduced turn-around-time, quality assurance costs, and system robustness.

17. The diagnostic laboratory system of claim 11, wherein the load plan indicates an assignment of all requested test types to at least some selected analyzers such that each selected analyzer has a substantially equal number of requested tests to be performed thereat.

18. The diagnostic laboratory system of claim 11, wherein the load plan indicates an assignment of all requested test types to at least some selected analyzers such that each selected analyzer has sufficient reagent to perform all requested tests assigned thereto.

19. A non-transitory computer-readable storage medium, comprising:

an optimization-based load planning module including a data-reduction scheme having computer-executable instructions configured to cause a computer server to:

create a number of load planning variables based on computer readable data concerning analyzers included in a diagnostic laboratory system, and test types and test numbers to be performed within the diagnostic laboratory system over a planning period, and preferences or priorities related to operation of the diagnostic laboratory system and to the test types and test numbers of the requested tests to be performed;

reduce the number of load planning variables by:

solving successive surrogate problems by, in a first phase of optimization, removing integer and binary constraints from most but not all load planning variables that are binary values or integer values; or representing common test order patterns of samples by meta-samples, each meta-sample representing more than one sample, and determining a first load plan for the meta-samples and then a final load plan with the remaining samples; or iteratively optimizing over successive time periods within the planning period including a first optimization for a first portion of the planning period and then a second optimization for a second portion of the planning period that includes the results of the first optimization; and determine a load plan for performing each of one or more requested test types over a planning period, the load plan comprising computer-executable instructions configured to cause a system controller to assign each of the requested test types to be performed over the planning period to one or more selected analyzers in accordance with one or more received preferences or priorities.

\* \* \* \* \*